(12) United States Patent
Remenar et al.

(10) Patent No.: US 8,410,287 B2
(45) Date of Patent: Apr. 2, 2013

(54) HYDRATED SODIUM SALT FORM OF CELECOXIB

(75) Inventors: Julius F. Remenar, Framingham, MA (US); Mark D. Tawa, Acton, MA (US); Matthew L. Peterson, Hopkinton, MA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 13/193,767

(22) Filed: Jul. 29, 2011

(65) Prior Publication Data
US 2012/0029205 A1 Feb. 2, 2012

Related U.S. Application Data

(60) Provisional application No. 61/369,295, filed on Jul. 30, 2010.

(51) Int. Cl.
*C07D 231/10* (2006.01)
*A61K 31/415* (2006.01)
(52) U.S. Cl. .................... 548/377.1; 514/406
(58) Field of Classification Search ................ 548/377.1
See application file for complete search history.

(56) References Cited

U.S. PATENT DOCUMENTS

| 7,790,905 B2 | 9/2010 | Tawa et al. |
| 7,927,613 B2 | 4/2011 | Almarsson et al. |

FOREIGN PATENT DOCUMENTS

| WO | WO 2004026235 A2 | 4/2004 |
| WO | WO 2004/061433 A1 * | 7/2004 |
| WO | WO 2004061433 A1 | 7/2004 |

OTHER PUBLICATIONS

International Search Report dated Sep. 13, 2011 for corresponding Application No. PCT/US2011/045839.
Remenar, J.F., Improving Oral Bioavailability Through Inhibitions of Crystallization After Dosing, Am. Pharm.Rev., 2007, 10, 84.
Guzman, H. R., et al., Combined Use of Crystalline Salt Forms and Precipitation Inhibitors to Improve Oral Absorption of Celecoxib from Solid Oral Formulations, J.Pharm.Sci., 2007, 96, 2686-2702.
Lu, G.W., et al., Characterization of a Novel Polymorphic Form of Celecoxib, J. Pharm. Sci., 2005, 95, 305-317.
Peterson, M.L., et al., Multi-component Pharmaceutical Crystalline Phases: Engineering for Performance, 2010, ch. 3, p. 67-99.
Paulson, S.K., et al., Pharmacokinetics of Celecoxib after Oral Administration in Dogs and Humans: Effect of Food and Site of Absorption, Pharmacol. Exp. Ther., 2001, 297, 638.
Gupta, P., et al., Physical Stability and Solubility Advantage from Amorphous Celecoxib: The Role of Thermodynamic Quantities and Molecular Mobility, Pharmacol., 2004, 1, 406.
Remenar, J.F., et al., Celecoxib:Nicotinamide Dissociation: Using Excipients to Capture the Cocrystal's Potential, Pharmacol., 2007, 4, 386-400.
Chen, L.R., Young, et al., Solid-State Behavior of Cromolyn Sodium Hydrates, J. Pharm. Sci., 1999, 88, 1191-1200.
Khankari, R., et al., Physical Characterization of Nedocromil Sodium Hydrates, J. Pharm. Sci., 1998, 87, 1052-1061.
Davey, R. J., et al., Structural and Kinetic Features of Crystal Growth Inhibition: Adlpic Acid Growing in the Presence of n-Alkanoic Acids, J.Chem.Soc., Faraday Trans., 1992, 88, 3461-3466.
Thompson, C., et al., The effects of additives on the growth and morphology of paracetamol (acetaminophen) crystals, Int. J. Pharm., 2004, 280, 137-150.
Weissbuch, I., et al., Crystal Morphology Control with Tailor-Made Additives; A Stereochemical Approach, Adv. Cryst. Growth Res., 2001, 381-400.
Dev, V.R., et al., Celecoxib, A COX-II Inhibitor, Acta Crystallogr., Sect.C: Cryst. Struct. Commun., 1999, 55, v, IUC990161.
Betteridge, P. W. et al., CRYSTALS version 12: software for guided crystal structure analysis, J. Appl. Cryst. 2003, 36, 1487.
Serajuddin, A.M., et al., Handbook of Pharmaceutical Salts, Verlag Helvetica Chimica Acta: Zürich and Wiley-VCH: Weinheim, 2002, ch. 6, pp. 138-139.
APEX2, Version 2 User Manual, M86-E01078, 40 Bruker Analytical X-ray Systems, Madison, WI, Jun. 2006.

* cited by examiner

*Primary Examiner* — Jason M Nolan
*Assistant Examiner* — Ana Z Muresan
(74) *Attorney, Agent, or Firm* — Laura A. Donnelly

(57) ABSTRACT

Hydrated celecoxib sodium salt forms and processes to prepare hydrated celecoxib sodium salt forms are disclosed. The celecoxib sodium salt forms are particularly useful and suitable for pharmaceutical applications.

2 Claims, 8 Drawing Sheets

HYDRATED SODIUM SALT FORM OF CELECOXIB

This application claims priority from a provisional filing, U.S. Ser. No. 61/369,295, filed on Jul. 30, 2010 entitled "Celecoxib Sodium Salts: Crystal Growth and Engineering for Performance".

FIELD OF THE INVENTION

The present invention relates to hydrated sodium salt forms of celecoxib and methods for their preparation. These salt forms are particularly well-suited for pharmaceutical applications.

BACKGROUND OF THE INVENTION

Creating supersaturated solutions of celecoxib "Cel" has been shown to increase the rate and extent of drug absorption.[2] Such increases offer the possibility of formulations using less drug and/or achieving faster pain relief from this COX-2 inhibitor. Combining a sodium salt of Cel with polyether surfactants was found to be particularly effective: the duration of supersaturation increased from less than one minute for the salt alone to greater than 60 minutes for the mixtures; plasma concentrations were higher after 30 minutes for the mixtures than they were after even 2 hours for the marketed formulation; and total drug absorption increased from around 40% to nearly 100%.[2] Since Cel is a weak acid with a pKa of 11.1,[14] its salts are neutralized rapidly in aqueous suspension at physiological pH (pH ~1-7), and the neutral drug crystallizes rapidly. Therefore, the observed improvements are believed to require both a starting form that cannot easily revert to the thermodynamically stable form of Cel (Cel-III) without first dissolving, and another molecule that will solvate the dissolved Cel to prevent or slow down the precipitation of Cel-III.

It has been shown that the bioavailability of Cel can be enhanced by dosing forms that are transiently more soluble than the marketed crystalline form, Cel-III.[1-4] The low solubility of Cel-III, limits both the rate and extent of absorption after dosing. Published strategies showing improvement in solubility and/or bioavailability of Cel have included co-crystals, salt forms, metastable polymorphs, amorphous dispersions and solutions in organic vehicles.[1-3, 7, 8] For example, U.S. Pat. No. 7,927,613 to Almarsson et al. discloses co-crystals comprising (1) celecoxib and nicotinamide and (2) celecoxib and 18-crown-6; and U.S. Pat. No. 7,790,905 to Tawa et al. discloses a propylene glycol solvate of a sodium salt of celecoxib, and in particular, a propylene glycol solvate of celecoxib sodium trihydrate.

Although it was known that the hydrated sodium salt of celecoxib gained and lost waters of hydration rapidly as a function of relative humidity "RH", there was no structural basis to understand this dynamic behavior. Sodium salts of other drug molecules with variable hydration behavior are known.[9,10] Several studies have shown "tailor-made" additives to successfully inhibit growth along specific crystal faces in order to modify habit.[11-13] A study by Davey et al. showed that the presence of alkanoic acids could modify the habit of the dicarboxylic acid, adipic acid. In this study, alcohols were added to crystallization media in an attempt to slow growth by inhibiting hydration of the sodium ion.

In accordance with the present invention, crystallization of the hydrated sodium salt of celecoxib with benzyl alcohol enabled structural determination of celecoxib sodium pentahydrate (Cel-Na($H_2O$)$_5$), a structure which proved useful to the understanding of the complex physical behavior of Cel-Na.

SUMMARY OF THE INVENTION

Crystalline salts forms of celecoxib (Cel) were prepared.

Hydrates of celecoxib sodium were prepared and characterized. The hydrate grows rapidly, forming a thick slurry of thin plates from aqueous alkaline solution. Crystals for structure determination were successfully grown by adding 1% benzyl alcohol to the solution.

The structure of the pentahydrate of the sodium salt is comprised of a bilayer motif where three waters are coordinated to sodium ions in a discreet layer while the other two waters reside in a one dimensional channel. The hydration state changes rapidly and reversibly as a function of relative humidity. The hydrated salt is physically stable in a sealed vial, but reverts rapidly to the crystalline free base if exposed to ambient $CO_2$ at 40% RH or higher.

Other features and advantages of the present invention will be apparent from the detailed description of the invention and from the claims.

DETAILED DESCRIPTION OF THE INVENTION

Figure 1:
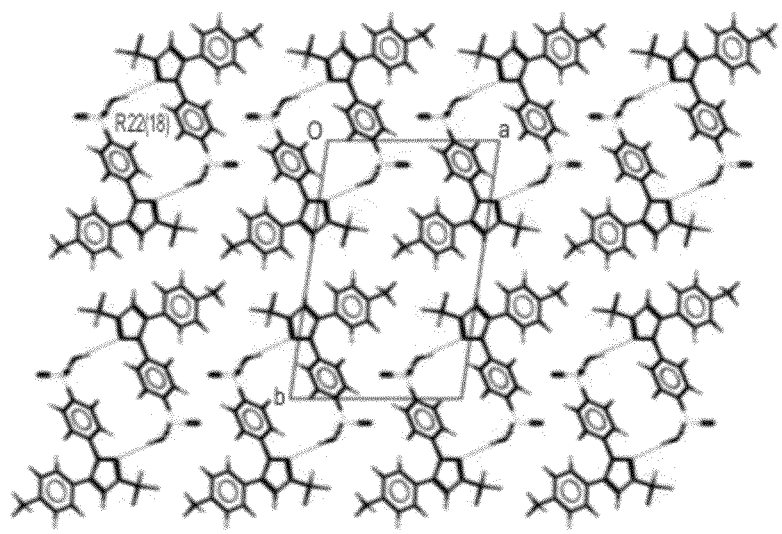
FIG. 1 shows a view of the packing of Cel-III dimers (R2/2(18)) which propagate along the a axis in crystallographic ab plane.

Materials and Methods.

Celecoxib was obtained from Matrix Labs and used for all experiments without further purification.

Preparation of Cel-Na($H_2O$)$_5$.

Bulk Material.

3.2 grams of celecoxib are dissolved in 32 mL of 1.0 N NaOH with gentle heating. Solubility is reduced by adding 1.0 mL of 2.5 N NaOH followed by subsequent addition of crystalline seeds of the hydrate. Without seeding, crystals will grow slowly over time. Crystallization is allowed to occur for 30 minutes at room temperature. The sample is then cooled in an ice bath for an additional 30 minutes and the crystals are collected by suction filtration and rinsed with 0.02 N cold NaOH (2×8 mL). The solids are allowed to dry for 1-2 minutes under suction on the filter and then transferred to a 20 mL scintillation vial. The vial is left open and stored inside of a 53% RH humidity chamber with low $CO_2$ until it reaches constant weight. Thereafter, the sample remains in the controlled humidity chamber, but with a cap for further protection. The humidity chamber is prepared ahead of time and consists of a dessicator, the bottom of which is filled with a supersaturated solution of Mg($NO_3$)$_2$. A 20 mL vial containing 2 mL of concentrated NaOH solution is left in the chamber to capture $CO_2$. The surface area of the NaOH solution is kept very small relative to the surface and volume of the salt solution so that it does not affect the humidity in the chamber.

Thicker Crystals of Cel-Na($H_2O$)$_5$.

1.3 grams of celecoxib are dissolved in 18 mL of 1.0 N NaOH and 50 uL of benzyl alcohol (0.3% v/v) are added. If a crystal for structure determination is required, it is important to avoid seeding effects. Crystallization slowly occurs over the course of up to five days. The crystals are isolated individually from the mixture. Seeding the solution will also produce high quality, thicker crystals as bulk Adding only 10 uL of benzyl alcohol fails to slow crystallization.

Preparation of Cel-NaPG($H_2O$)$_3$.

1.55 grams of Cel-III were dissolved in 5.0 mL of 1.0 N NaOH and 0.65 mL of PG was added. 0.90 ml, of 2.5 N NaOH was added, causing precipitation. The suspension was warmed gently to re-dissolve the solids, the solution was filtered into a clean vial, seeds were added, and the suspension was sonnicated for 10 seconds. On standing and cooling, the slurry became a thick paste over 5 minutes. The sample was cooled in an ice bath for 5 minutes, then filtered by suction filtration and rinsed with 0.02 N NaOH in water containing 5% PG (2×2.0 mL). The thick paste filtered slowly and was left covered under vacuum for 1 hour. The paste remains damp after this treatment. The wet solids were suspended in 5 mL of t-butylmethylether for 1 minute and suction filtered before drying in a vacuum oven at room 35 temperature for 30 minutes with a flow of air through the oven. The drying was stopped twice to break up clumps with a spatula, which ultimately yielded a dry powder.

Preparation of Cel NaPG.

A scintillation vial containing 1.5 grams of Cel NaPG ($H_2O$)$_3$ was placed in a vaccuum oven at 50° C. for 2 hours and then transferred to an 80° C. oven for 1 hour. The compound melted in the 80° C. oven but crystallized from the melt upon cooling, which removes only some of the water. The residual Cel NaPG($H_2O$)$_3$ can be removed by suspending the solid mixture in t-butylmethylether, filtering, and drying for 1.5 hours in a vacuum oven at 50° C. Up to two suspension cycles may be necessary to effectively remove all Cel NaPG ($H_2O$)$_3$. In addition, Cel NaPG can be directly crystallized from diethyl ether in the presence of greater than one equivalent of propylene glycol by addition of one equivalent sodium ethoxide. Crystals grow immediately upon addition of base. The product is isolated by filtration and washed by additional diethyl ether to remove any excess propylene glycol.

Powder X-ray Diffraction (pXRD)—Rigaku Capillary Transmission Instrument.

X-ray powder diffraction patterns are obtained using the D/Max Rapid X-ray Diffractometer equipped with a copper source (Cu/K1.54056 Å), manual x-y stage, and 0.3 mm collimator. A sample is loaded into a 0.3 mm boron rich glass capillary tube by sectioning off one end of the tube and tapping the open, sectioned end into a bed of sample. The loaded capillary is mounted in a holder that is secured into the x-y stage. A diffractogram is acquired under ambient conditions at a power setting of 46 kV at 40 mA in transmission mode, while oscillating about the ω-axis from 0-5° at 1°/sec and spinning about the Φ-axis at 2°/sec. The exposure time is 5 minutes unless otherwise specified. The diffractogram obtained is integrated over 2-θ from 2-40° and χ (1 segment) from 0-360° at a step size of 0.02 using the cylint utility in the RINT Rapid display software provided with the instrument. The dark counts value is set to 8 as per the system calibration; normalization is set to average; the ω offset is set to 180°; and no χ or Φ offsets are used for the integration.

Bruker D8 Discover pXRD Diffractometer.

X-ray powder diffraction patterns are obtained using the Bruker AXS D8 Discover X-ray Diffractometer equipped with GADDS™ (General Area Diffraction Detection System), a Bruker AXS HI-STAR Area Detector at a distance of 15.05 cm as per system calibration, a copper source (Cu/Kα 1.54056 Å), automated x-y-z stage, and 0.5 mm collimator. A sample is compacted into pellet form and mounted on the x-y-z stage. A diffractogram is acquired under ambient conditions at a power setting of 40 kV and 40 mA in reflection mode while the sample remains stationary. The exposure time is 5 minutes unless otherwise specified. The diffractogram obtained undergoes a spatial remapping procedure to account for the geometrical pincushion distortion of the area detector, then is integrated along χ from −118.8 to −61.8° and 2-θ 2.1-37° at a step size of 0.02° with normalization set to bin normalize. Diffraction patterns obtained on the Bruker machine are viewed using DIFFRAC$^{Plus}$ Evaluation software.[3]

DVS

Moisture sorption analysis was performed using a Dynamic Vapor Sorption apparatus (Surface Measurement Systems, Monarch Beach, Calif.). Each sample was placed in a clean glass crucible and equilibrated in the apparatus at a specified RH level. Varying the flow rates of dry nitrogen gas and saturated wet nitrogen gas streams controlled RH; the total combined flow rate was kept constant at 200 standard cubic meters per minute. After initial equilibration, RH was varied and change in mass was recorded over time as an indication of moisture sorption. Mass equilibration at each humidity level was determined as a change in mass less than $\pm 2 \times 10^{-5}$ grams over a time interval of 1 minute (dm/dt of 0.002% min). After the assay, the change in mass was mathematically converted to water molar equivalents per dry compound molar equivalent.

Scanning Electron Microscopy (SEM).

Crystals were analyzed using a Fenom FEI Scanning Electron Microscope. Samples were mounted onto an SEM sample holder using carbon tape and sputter-coated with a thin gold layer. Each sample was scanned at a medium level of magnification to understand the character and size distribution of the crystals. Images were captured at magnification up to 10 000×.

Proton Nuclear Magnetic Resonance Spectroscopy ($^1$H NMR)

$^1$H NMR measurements were conducted using a Varian 400 MHz spectrometer with averaging of 128 scans. Samples were prepared as 10 mg/ml solutions of Cel in $CDCl_3$.

X-Ray Data Collection, Solution, and Refinement for Cel-Na$(H_2O)_5$.

All operations were performed on a Bruker-Nonius Kappa Apex2 diffractometer, using graphite-monochromated MoK radiation. All diffractometer manipulations, including data collection, integration, scaling, and absorption corrections were carried out using the Bruker Apex2 software.[15] Preliminary cell constants were obtained from three sets of 12 frames. Data collection was carried out at 150K, using a frame time of 20 sec and a detector distance of 37.5 mm. The optimized strategy used for data collection consisted of Φ and ω scan sets, with 0.5° steps in Φ or ω; completeness was 99.7%. A total of 1485 frames were collected. Final cell constants were obtained from the xyz centroids of 9276 reflections after integration. From the systematic absences, the observed metric constants and intensity statistics, space group P21/c was chosen initially; subsequent solution and refinement confirmed the correctness of this choice. The structure was solved using direct methods programs in the Apex2 software.[1] The structure was refined (full-matrix-least squares) using the Oxford University Crystals for Windows program.[16] All non-hydrogen atoms were refined using anisotropic displacement parameters. The H atoms were initially refined with soft restraints on the bond lengths and angles to regularize their geometry (C—H in the range 0.93-0.98, N—H in the range 0.86-0.89, O—H=0.82 Å and $U_{iso}$(H) in the range 1.2-1.5 times $U_{eq}$ of the parent atom), after which the positions were refined with riding constraints. The final least-squares refinement converged to $R_1$=0.0431 (I>2σ (I), 13 607 data) and $wR_2$=0.1163 (F2, all 17 621 data, 580 parameters). The data establish the material as a pentahydrate of the sodium salt of celecoxib (Cel-Na$(H_2O)_5$).

Results and Discussion.

Improving the absorption of Cel requires a shelf-stable form that will resist conversion to the poorly soluble polymorph Cel-III following dosing.[1,3,4] Our approach requires a form where the packing motifs observed in Cel-III have been disrupted. In the presence of polyethers, the crystallization of Cel-III is inhibited and results in increased in vivo exposure. Analysis of the packing diagram for Cel-III[14] reveals that the structure is comprised of head-to-tail, R2/2(18), celecoxib dimers which propagate along the a axis.

Figure 2:
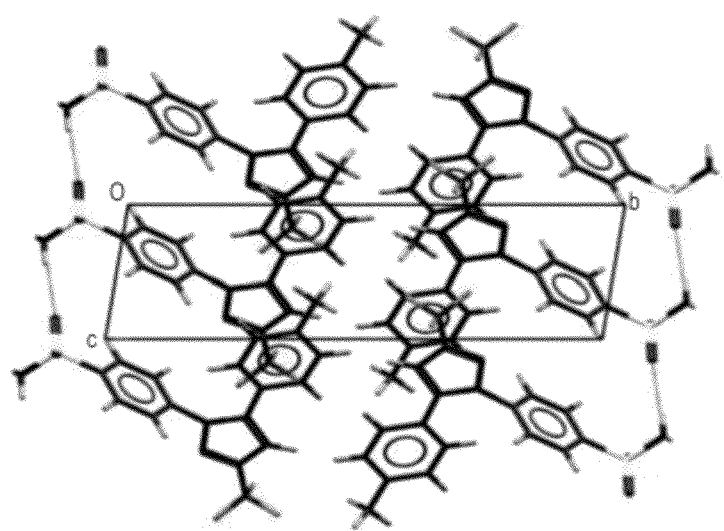
FIG. 2 shows a view of packing of Cel-III chains (C4) which propagate along the c axis in crystallographic bc plane.

Additional hydrogen bonding consisting of sulfonamide chains (C(4)) which propagate along the c-axis are shown in FIG. 2.

Crystal Growth and Physical Characterization of Sodium Salt Hydrates.

The formation of pharmaceutically acceptable celecoxib salts is limited by the high acid dissociation constant of the sulfonamide group (pKa~11.1[6]). The standard guideline for salt preparation suggests choosing bases with a pKa at least 2 units higher than the acid[17]. Since no pharmaceutically acceptable bases have a pKa>13.1, attempts to make a salt of celecoxib focused on the use of excess sodium hydroxide in aqueous solutions having pH over 12. While the aqueous solubility of celecoxib at physiological pH is <0.5 μg/ml[3], approximately 380 mg/ml concentration of celecoxib was achieved in alkaline solutions at room temperature. Evaporation of these solutions to dryness under nitrogen yielded the first crystalline materials, but it was subsequently found that allowing the solutions to stand overnight would also yield single crystals of Cel-Na$(H_2O)_5$. The crystallization can be accelerated and the yields improved by cooling in an ice bath or by addition of sodium chloride.

Figure 3:
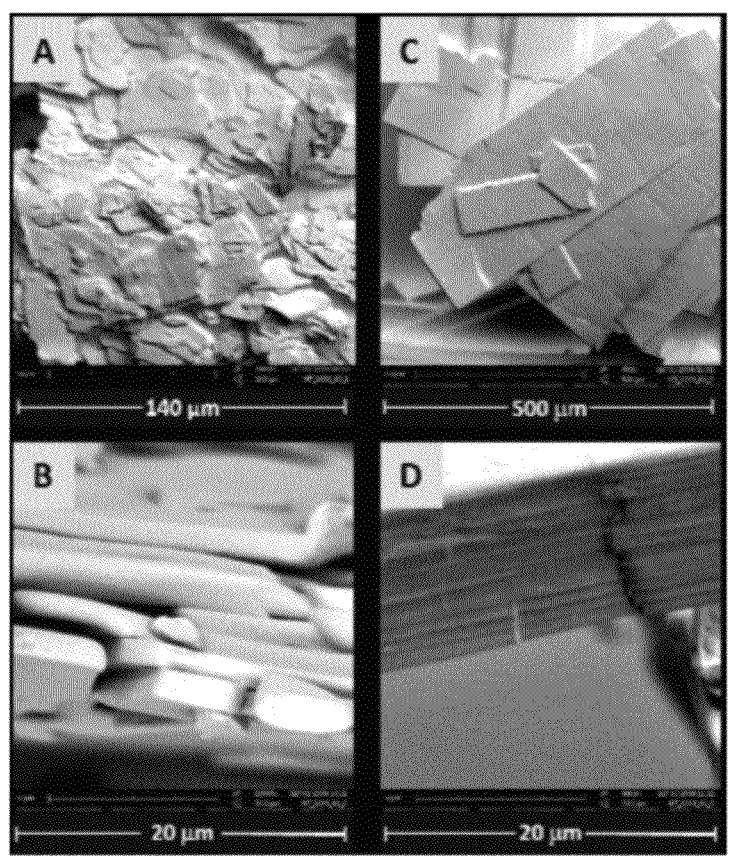
FIG. 3 shows SEM images of Cel-Na($H_2O$)$_5$ grown from 1.0 N NaOH (A and B) and 1.0 N NaOH+0.3% benzyl alcohol (C and D).

Crystallization from aqueous NaOH with or without added NaCl yielded crystalline plates that were typically less than 2 um thick (FIGS. 3A and 3B). While larger plates could be grown by changing temperature, sodium content, and Cel concentration, the thickness never increased appreciably, leaving material that was difficult to collect and unsuitable for structure determination by single crystal X-ray. Since sodium ions are generally solvated and Cel-Na$(H_2O)_5$ has rich hydration behavior, it was reasoned that a competing —OH group from an alcohol co-solvent might interfere with hydrate ordering during crystallization, thereby slowing the rapidly growing faces of the plane and allowing thicker crystals to form. Varying levels of methanol, ethanol, and benzyl alcohol were added to the crystallization from NaOH; 2-propanol and propylene glycol were not added as they were shown to form solvates with Cel-Na in early form screening studies. 0.3-1% benzyl alcohol was found to inhibit the crystallization, sometimes for several days while the remaining alcohols had little effect. The crystals grown in the presence of benzyl alcohol were larger than 10 um in all dimensions, as shown in FIGS. 3C and 3D.

Structure Description for Cel-Na$(H_2O)_5$.

Figure 4:
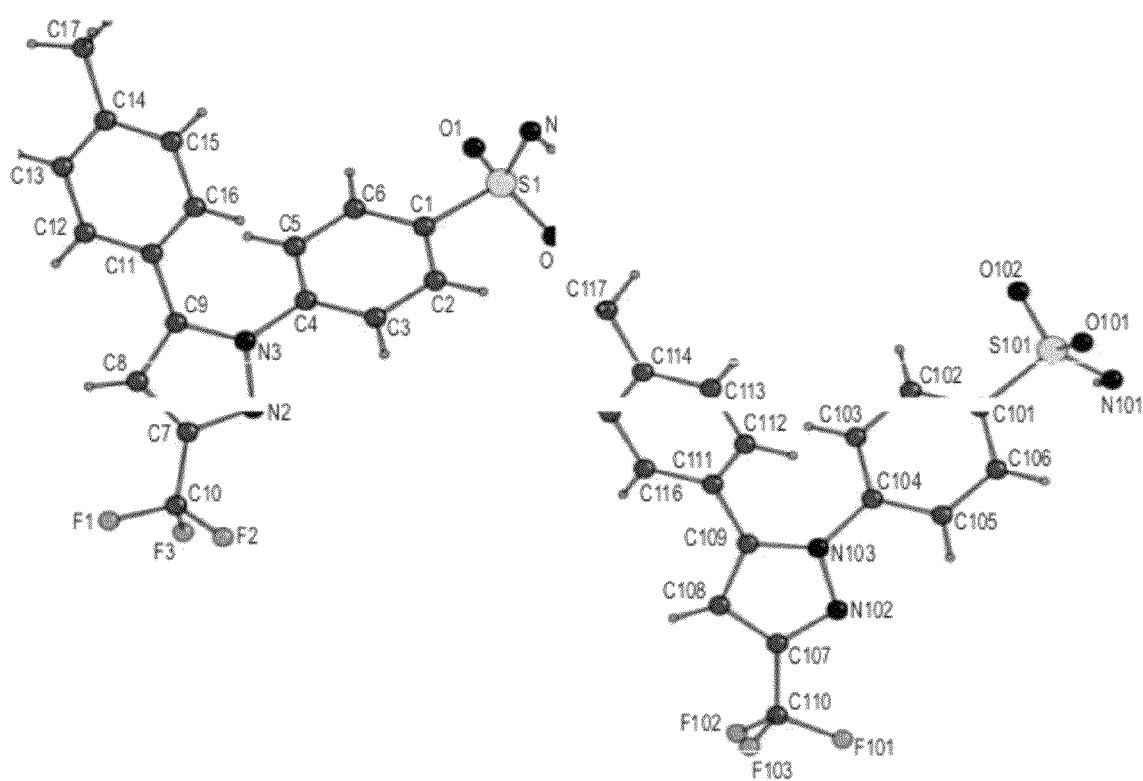
FIG. 4 shows a view of the two independent celecoxib anions in CelNa$_5$H$_2$O, showing labeling scheme for the Cel anions (50% probable ellipsoids). Na and water oxygen atoms are not shown, but are well ordered, with Ueq of water O at 0.03+/−0.01 (cf. carboxylate O at 0.021+/−0.006 Å$^2$). The molecules are conformationally similar, with the largest difference in torsion angles being that between N102-N103-C104-C105 (37.1°) and N2-N3-C4-C3 (44.9°).
Figure 5:
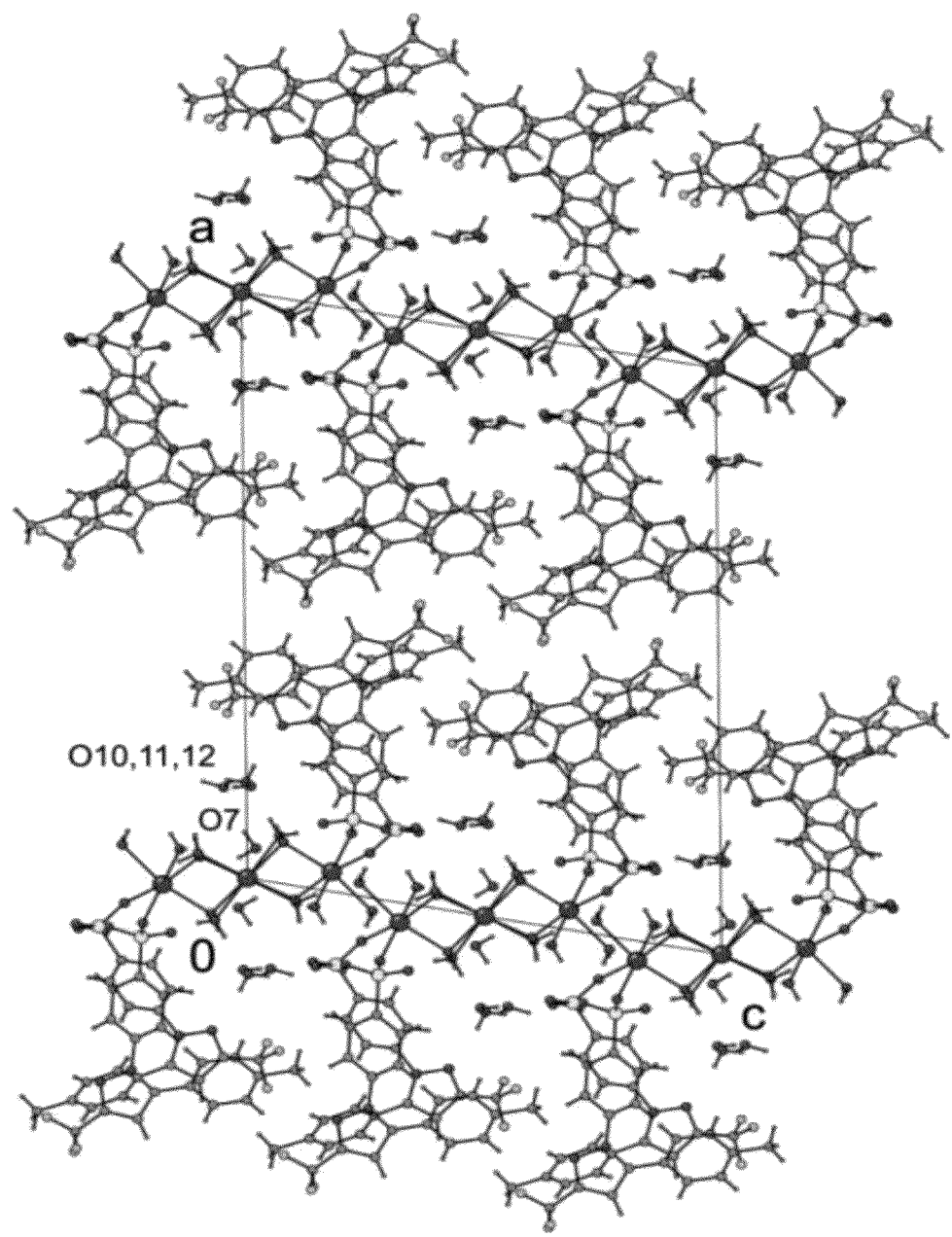
FIG. 5 shows a view of Cel-Na($H_2O$)$_5$, showing the packing of molecules along the b axis. The bilayer-type crystal structure consists of a hydrogen bonded sodium coordination polymer layer, which blankets two layers of celecoxib anions, all in crystallographic bc planes.

The crystal structure of Cel-Na$(H_2O)_5$ has been solved and confirms its composition as a pentahydrate. Crystallographic data for Cel-Na$(H_2O)_5$ is shown in Table 1 with a view of the two independent celecoxib anions shown in FIG. 4. Inspection of the packing diagram indicates that the material is comprised of a bilayer-type crystal structure consisting of a hydrogen bonded sodium coordination polymer layer, which blankets two layers of celecoxib anions, all in crystallographic bc planes (FIG. 5).

Figure 6:
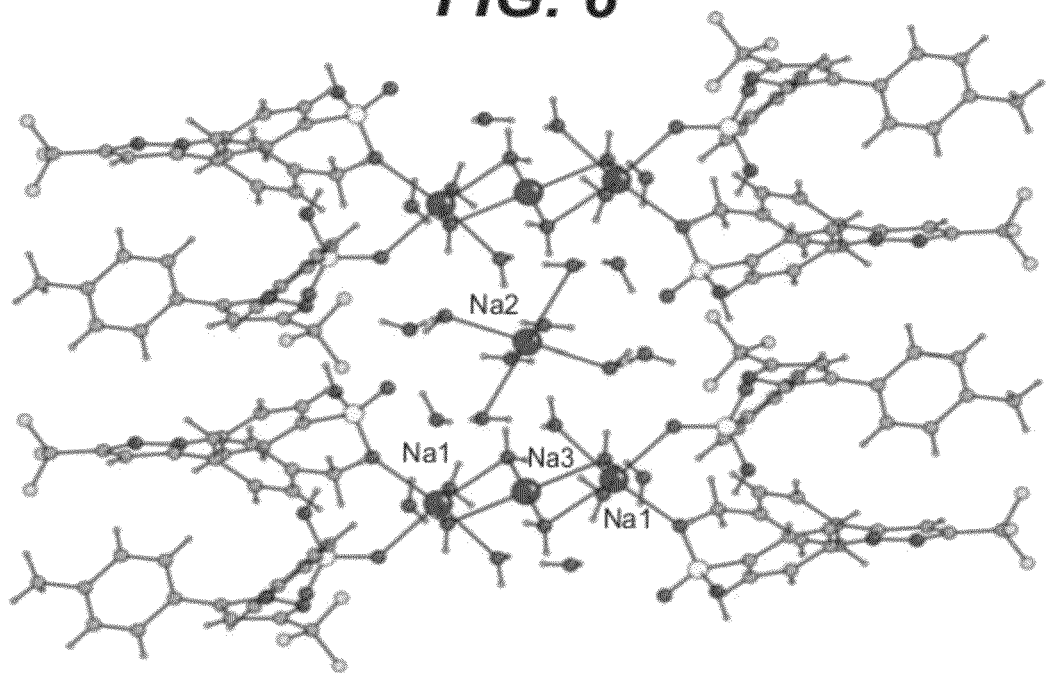
FIG. 6 shows a view of Cel-Na($H_2O$)$_5$ layers, emphasizing sodium ion coordination and how atoms Na2 and Na3 are six-coordinate, bonding only to water molecules. Atoms Na2 and Na3 reside on centers of symmetry at (0 0 0) and (0 ½ 0), respectively.

The stoichiometry was established as a pentahydrate of the sodium salt with atom Na1 residing on a general position and coordinating to the sulfonamide anion, and atoms Na2 and Na3 which are six-coordinate, bonding only to water molecules, as shown in FIG. 6. Atoms Na2 and Na3 reside on centers of symmetry at (0 0 0) and (0 ½ 0), respectively. Further analysis of the unit cell confirms that 6 water molecules are coordinated to the sodium atoms, with the remaining 4 hydrogen bonded within a channel in the structure, also shown in FIG. 5. Atoms O7, O10, O11, O12 are not bonded to Na. O8, O9, O3, O4, O6 and O5 are coordinated to Na atoms. Specifically, the six oxygen atoms coordinated to Na have Na—O distances ranging from 2.32-5 2.43 Å. Of the four non-coordinated oxygen atoms, none is closer to Na than 3 Å, except for O7 (distance to Na2 of 2.68 Å and Na3 of 2.59 Å), resulting in a very weak interaction to Na for O7. Water molecules corresponding to O10, O11, O12 are all H bonded to each other, and O7 is H-bonded to O12. 10 O10, O11 and O12 are in one dimensional channels, centered at ca. (0.157, y, −0.013) and others related by symmetry. O7 is located at the edge of the channel at (0.053, 0.744, 0.019).

TABLE 1

Crystallographic Data for Cel-Na(H$_2$O)$_5$

| | |
|---|---|
| Chemical formula | C$_{17}$H$_{13}$F$_3$N$_3$O$_2$S$_1$Na$_1$·5H$_2$O |
| Formula weight | 986.87 g/mol |
| Temperature | 150(1) K |
| Wavelength | 0.71073 Å |
| Crystal size | 0.042 × 0.400 × 0.733 mm |
| Crystal system | monoclinic |
| Space group | P2$_1$/c (No. 14) |
| Unit cell dimensions | a = 25.9317(14) Å |
| | b = 9.0340(5) Å |
| | c = 19.4396(10) Å |
| | β = 100.535(2)° |
| Volume | 4477.3(4) Å$^3$ |
| Z, Z' | 8, 2 |
| Density (calculated) | 1.464 Mg/m$^3$ |
| Final R indices | data; I > 2.0σ(I) R$_1$ = 0.0431, wR2 = 0.1065 |
| | all data R$_1$ = 0.0623, wR$_2$ = 0.1163 |

Hydration States of Cel-Na(H$_2$O)$_x$.

Despite clear assignment of Cel-Na(H$_2$O)$_5$, the molecule will be described as Cel-Na(H$_2$O)$_x$, except when specific hydration states are being discussed, because the pentahydrate exists only in the presence of bulk water or when kept cold. Indeed, understanding the behavior of the salt form before the single crystal structure was solved was challenging in that the powder patterns seemed to change almost daily, even when powders were equilibrated in humidity chambers prior to measurement. It was only through a combination of techniques including single crystal and powder diffraction as well as DVS that a more complete understanding of the hydration behavior of the celecoxib sodium salt could be attained. Consistent powder patterns were obtained by two distinct methods. In the first method, powder was filled into 0.5 mm capillary tubes, equilibrated in controlled humidity chambers for 1 week, sealed with silicone grease immediately upon removal from the humidity chambers, and measured immediately with a transmission powder X-ray diffractometer. In the second, a sample was monitored by a reflectance mode powder X-ray diffractometer fitted with a controlled humidity stage. The two methods were complimentary. The capillary method provided high resolution patterns without preferred orientation effects. However, the humidity control was coarse and was limited to conditions that could be achieved with standard saturated salt solutions. The controlled humidity PXRD stage showed fewer, more intense peaks, but the measurements were made in increments of 5% relative humidity, during both hydration and dehydration.

Figure 7:
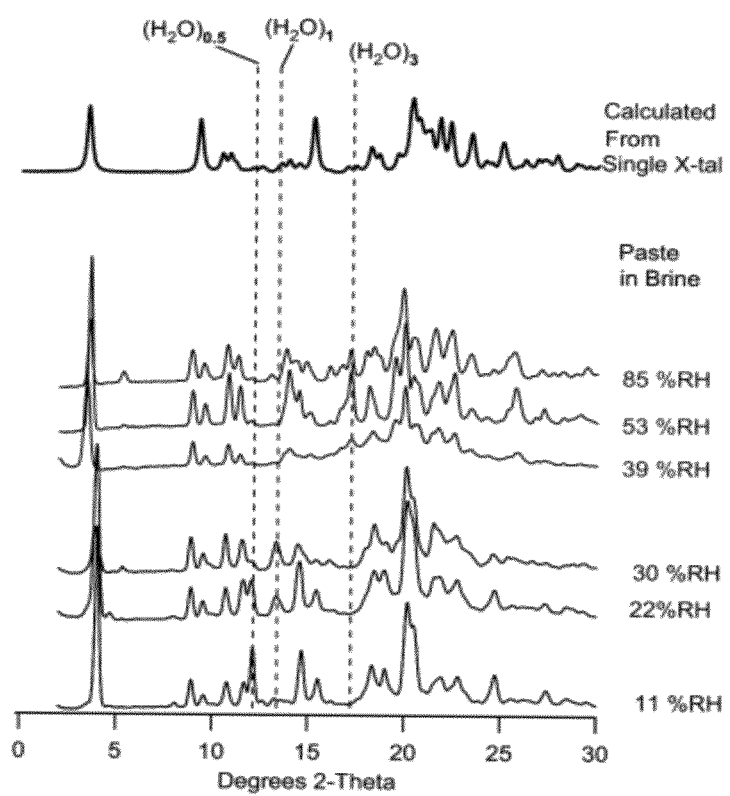
FIG. 7 shows PXRD patterns measured by transmission PXRD after packing samples into capillary tubes, equilibrating them in controlled RH chambers, and sealing the tops with silicone grease to prevent changes moisture exchange during the measurement.

The data obtained from the transmission powder X-ray diffractometer are illustrated in FIG. 7. The overlay of the powder patterns indicates that an increase in the shift of the peak at ~3.6 2-θ is observed when the material is subjected to decreased humidity conditions. Additionally, peaks representing the different hydration states become apparent as shown in FIG. 7. A sample removed from a humidity chamber kept at ~11% RH shows a peak at 12.1 2-θ corresponding to the hemihydrate, Cel-Na(H$_2$O)$_{0.5}$. When humidity is increased (up to 30% RH) this peak begins to disappear with emergence of a new peak at 13.4 2-θ, corresponding to a monohydrate, Cel-Na(H$_2$O)$_1$. Material stored between 40-85% RH results in the emergence of peaks at 17.2 and 25.8 2-θ for the trihydrate, Cel-Na(H$_2$O)$_3$, and the pattern remains largely unchanged when compared to a sample removed from a brine solution which is believed to correspond to the pentahydrate, Cel-Na(H$_2$O)$_5$.

Figure 8:
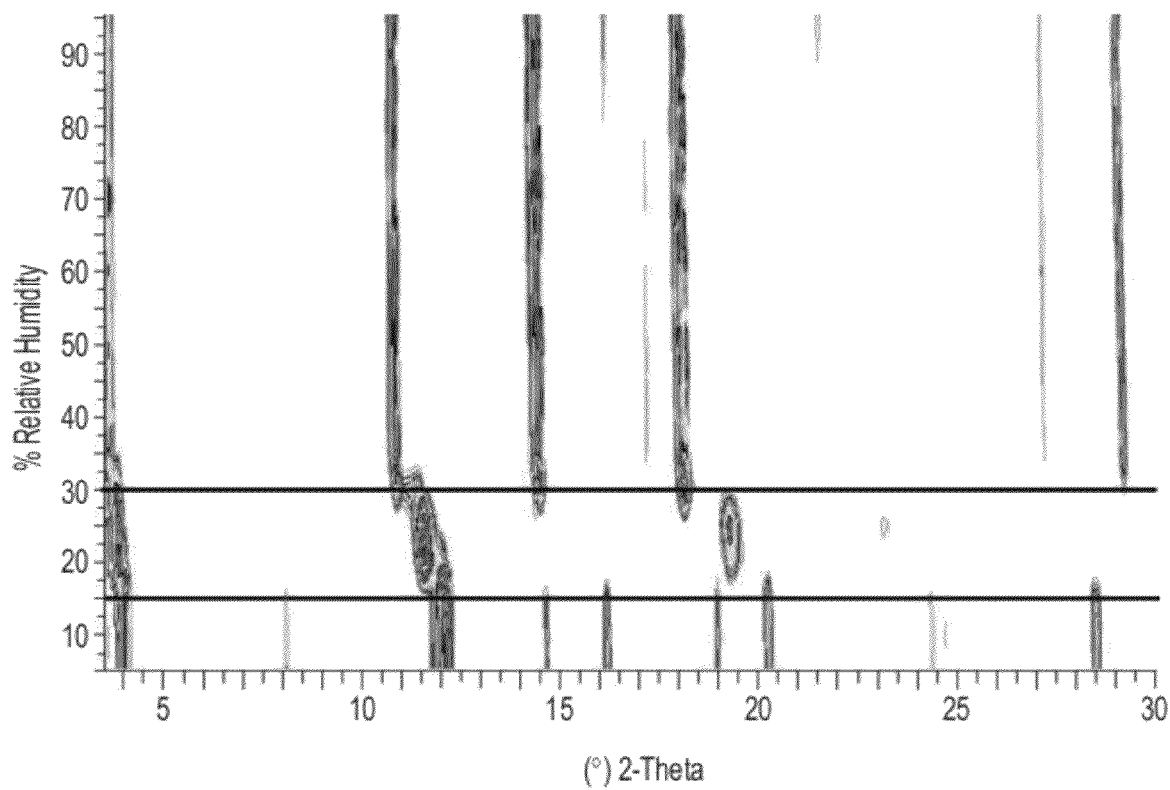
FIG. 8 shows PXRD pattern peak intensity map vs. % RH at 25° C. for a sample of Cel-Na($H_2O$)$_x$ in controlled humidity chamber of a reflectance mode powder diffractometer.
Figure 9:
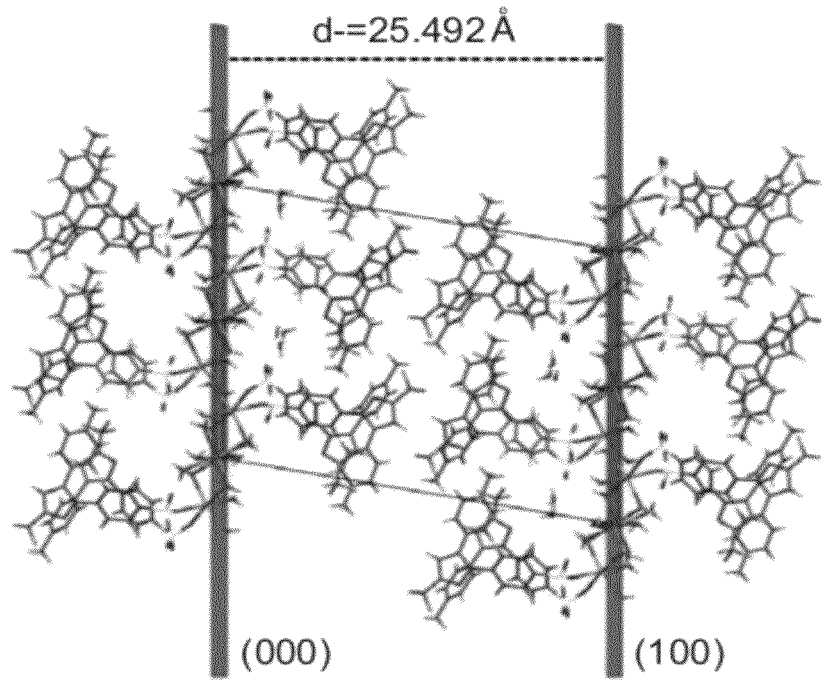
FIG. 9 shows a view of the packing diagram for Cel-Na($H_2O$)$_5$ with the (100) family planes drawn, indicating the distance of 25.492 Å between the planes. Loss of water from the sodium coordination polymer is expected to result in a decrease in the distance between bilayers along the a-axis. Loss of water from the channel is not expected to result in a measurable change in the crystal packing as supported by PXRD patterns taken as a function of humidity (see FIGS. 7 and 8).

A two-dimensional plot of peak intensity vs. relative humidity from the reflectance mode powder X-ray diffractometer fitted with a controlled humidity stage is illustrated in FIG. 8. Examination of the changes in the PXRD patterns as a function of decreased humidity indicates that several peaks shift to higher 2-θ values. The shift is most pronounced from ~35% to ~4% RH with minimal change at humidities above 30% RH. For example, the d-spacing for the peak at ~3.5 2-θ, corresponding to a planar spacing at (100) decreases with lower humidity. The shift is consistent with the bilayers moving closer to one another in the direction of the longest-axis (a), and may be impacted most significantly by water loss from the sodium ion layer, as shown in FIG. 9. While a complete mechanistic study is required to determine the full structural impact of hydration/dehydration of Cel-Na(H$_2$O)$_x$, the PXRD data do suggest that water molecules lost from the channel will result in less significant changes to the unit cell compared to those coordinated to sodium.

Figure 10:
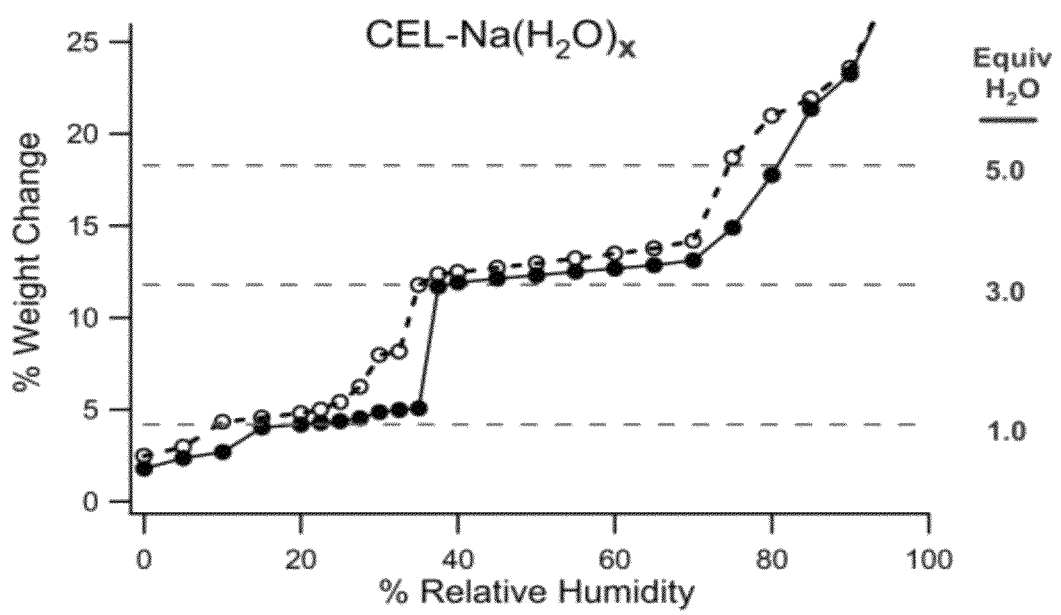
FIG. 10 shows a Dynamic Vapor Sorption "DVS" of Cel-Na($H_2O$)$_x$ at 25° C. 1.8% wt was added to all points to account for estimated residual water at 0% RH and to make weights consistent with a mono and trihydrate at the plateaus, as described in the text.

The hydration of celecoxib sodium was additionally studied using DVS at 25° C. and the data are illustrated in FIG. 10. The hydration is reversible throughout the full humidity range with some hysteresis at the transition points. There are two major plateau regions in the DVS profile. The first plateau between 40 and 70% RH is believed to correspond to a trihydre of the celecoxib sodium salt. Given that the single crystal and PXRD data suggest that a trihydrate is likely to exist and that a stable trihydrate would contain 11.8% water, a value of 1.8% weight is added to all points and is likely due to residual water at 0% RH. The smaller plateau between 15-30% RH is separated from the trihydrate plateau by 7.8% weight, or two water molecules indicating the likely existence of a monohydrate. The other final unique region as identified by VH-PXRD is between 0-10% RH which is consistent with a hemihydrate. The water content of Cel-Na(H$_2$O)$_x$ continues to change above 70% RH, without a clear stable region for the pentahydrate. In summary, the three hydration states observed by DVS correspond to: a hemi-hydrate below 10% RH; a monohydrate from 20-30% RH and a trihydrate from 40-70% RH. It is difficult to directly measure the amount of water remaining in a 0% RH DVS pan or in the controlled humidity PXRD stage, because opening the sample chamber to collect the samples for techniques such as TGA or Karl-Fisher titration exposes the samples to atmospheric moisture, and water uptake by Cel-Na is rapid.

Instability of Cel-Na(H$_2$O)$_x$ Toward Air.

Figure 11:
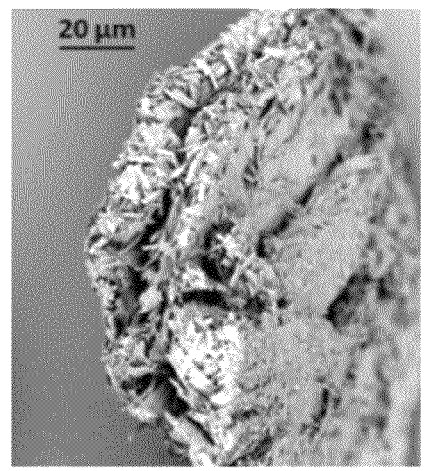
FIG. 11 shows a SEM image of Cel-Na($H_2O$)$_5$ indicating the growth of Cel-III on the outside of the crystals.

Cel-III begins to appear in samples that are left exposed to the air, as was initially seen by the peak at 7.9 2-θ in the PXRD patterns of samples stored in humidity chambers (see FIG. 8). The neutralization of the salt increases at high humidity and was shown to result from reaction with CO$_2$ and water in air. The behavior was first observed when using compressed air instead of nitrogen in the dynamic vapor sorption experiment, but it was also clear in samples stored open in controlled humidity chambers. The neutralization was minimized to get clean PXRD patterns by including small vials of concentrated NaOH solution within the closed humidity chambers to remove CO$_2$ from the air. An SEM image, shown in FIG. 11, shows formation of crystalline Cel-III on the outside of Cel-Na($H_2O$)$_5$ crystals due to neutralization. Throughout the conversion, both Cel-III and the sodium salt are clearly observed by PXRD with Cel-III growing slowly over time. Cel-III peaks emerge without appreciable broadening of the PXRD patterns for the salt, indicating that the conversion occurs primarily at the surface rather than throughout the crystal by infiltration of $CO_2$ into the channels.

Propylene Glycol (PG) Solvate of the Sodium Salt.

Alternative solvates were sought in an attempt to improve the physical stability of Cel-Na, both with respect to changes in mass vs. relative humidity, and to improve the stability in air. After an initial screen yielded a hydrated 2-propanol solvate, it was rationalized that propylene glycol might have several advantages: it has two hydroxyl groups that could solvate sodium ions; it has a high boiling point (187° C.); and it is commonly used in pharmaceutical formulations. Two PG solvates were found: an anhydrous solvate (Cel-NaPG) and a trihydrated PG solvate (Cel-NaPG($H_2O$)$_3$). Most importantly, Cel-NaPG($H_2O$)$_3$ resists conversion to neutral Cel compared to Cel-Na($H_2O$)$_x$; no conversion was observed after 4 days at 45 66% RH. Cel-NaPG($H_2O$)$_3$ is isolated from aqueous sodium hydroxide solutions of Cel containing at least one equivalent of PG. The anhydrous form, 1-NaPG, is prepared from the trihydrate by removing the water of hydration in a vacuum oven at 45-55° C. and heating the dehydrated powder to 80° C. for 20-30 minutes. Cel-NaPG can also be crystallized from alkaline solutions of celecoxib in diethyl ether containing greater than one equivalents of PG. TGA data show that PG is retained in Cel-NaPG until approximately 80° C. under a flow of nitrogen.

Figure 12:
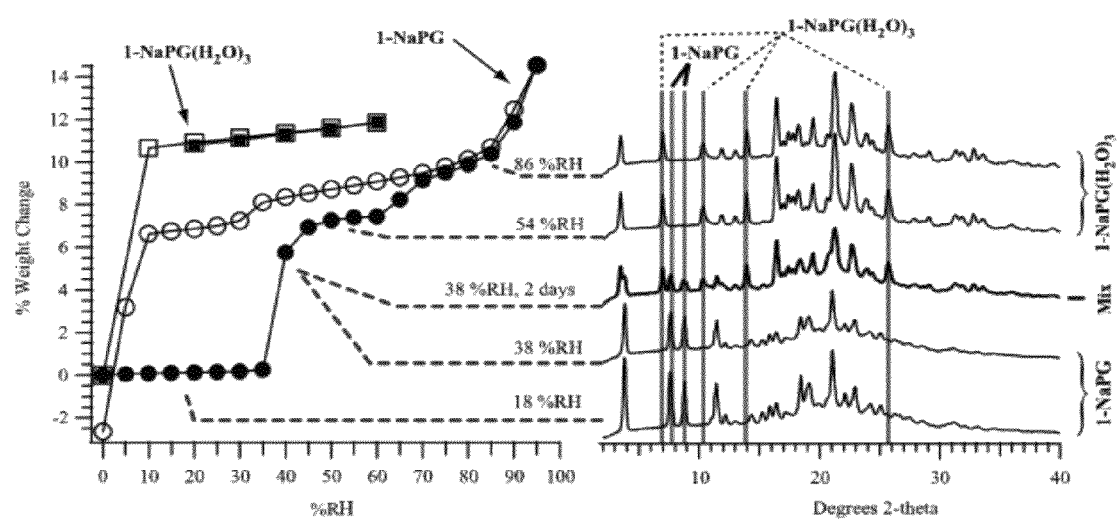
FIG. 12 shows DVS profiles of a sample of Cel-NaPG and Cel-NaPG($H_2O$)$_3$ at 25° C.(left), and PXRD patterns for samples of 1-NaPG equilibrated in controlled humidity chambers for 1 or 2 days at room temperature. Cel is represented as 1 in the figures. Solid symbols in the DVS profile mark the adsorption cycles, hollow symbols mark the desorption profiles. The labels to the right of the PXRD patterns indicate the form assignment. The vertical grey lines and labels above highlight some characteristic peaks for each form. The % RH values given to the left of the PXRD patterns refer to the humidity of the chamber in which the samples were equilibrated.

The conversion between Cel-NaPG and Cel-NaPG($H_2O$)$_3$ was found to be much less facile than changes in water content within Cel-Na($H_2O$)$_x$. The dynamic vapor sorption profiles were measured starting with Cel-NaPG at 0% RH, and for Cel-NaPG($H_2O$)$_3$ beginning at 20% RH to avoid dehydrating it prior to the first absorption cycle. The profiles are shown in FIG. 12 alongside PXRD patterns for samples of Cel-NaPG stored in controlled humidity chambers for 1-2 days. The dynamic profiles differ significantly depending on the starting material, suggesting that they do not reflect equilibrium behavior. Cel-NaPG($H_2O$)$_3$ is relatively non-hygroscopic between 10 and 70% RH at 25° C., reversibly gaining 1.2% weight. In contrast, Cel-NaPG shows complex behavior, gaining nearly 14% weight during adsorption and ending with a partial loss of PG after desorption. There are two major differences between the two profiles that must be explained. First, Cel-NaPG and Cel-NaPG($H_2O$)$_3$ both appear to be physically stable from 10-40% RH in the dynamic profile, while only one of them can be the thermodynamically stable form at a given water activity. Second, Cel-NaPG is already anhydrous at the beginning of the experiment, but it loses an additional 2% weight after going through the entire profile.

Samples of each form were stored in controlled humidity chambers and monitored for at least 1 week to determine which one is physically stable at each % RH. Cel-NaPG ($H_2O$)$_3$ is formed from samples of Cel-NaPG when stored at 18% RH or higher, showing that the trihydrate is the more stable form over a very wide humidity range. The rate of conversion to Cel-NaPG($H_2O$)$_3$ is very slow at 18% RH and increases to the point where conversion takes less than one day at 54% RH or higher. TGA shows that Cel-NaPG gains about 2 equiv of water within 1 day when stored in a 38% RH chamber but peaks associated with Cel-NaPG($H_2O$)$_3$ only begin to appear after the second day, as detected by PXRD. A sample of Cel-NaPG($H_2O$)$_3$ showed no conversion to Cel-NaPG after 4 days of storage over the 18% RH salt bath, indicating resistance to dehydration.

The loss of dry-weight from Cel-NaPG during the DVS experiment suggested that the PG could be labile, a property that could contribute to instability. Samples subjected to multiple humidity cycles were found to lose additional weight after each cycle, and the profiles began to look more like Cel-Na($H_2O$)$_x$. However, no loss was seen when starting with Cel-NaPG($H_2O$)$_3$ at 20% RH and subjecting it to a single humidity cycle. Increased lability and loss of PG during the transition from anhydrous to trihydrate was believed to be the most likely explanation for the weight loss. $^1$H NMR was used to determine whether the PG solvate is lost continuously throughout the humidity cycle or only during change in the hydration state. Cel-NaPG and Cel-NaPG($H_2O$)$_3$ were exposed to 0% RH and 40% RH in the DVS and then dissolved in methanol-d4 for NMR analysis. The Cel:PG ratio was stable at 1/1 for Cel-NaPG($H_2O$)$_3$ after treatment for either four hours at 40% RH or 18 hours at 0% RH. However, Cel-NaPG lost 8.2% PG over four hours at 40% RH, while remaining stable under a stream of dry nitrogen for 18 hours (0% RH). Since the Cel-NaPG($H_2O$)$_3$ has a wide range of physical stability, conversion from the trihydrate to the anhydrous and then back to the trihydrate should be a rare event. In a closed system such as a packaged tablet, PG should not be lost as easily as it is in the dynamic environment of the DVS where gases continuously flow over the sample to carry away any volatile components.

CONCLUSION

Celecoxib sodium salt forms have been studied. Cel-Na exists as a pentahydrate when suspended in aqueous alkaline media. Addition of 1% benzyl alcohol facilitated the growth of crystals sufficiently large for structure determination by single X-ray diffraction. The salt crystallizes in a bilayer structure having layers of celecoxib and layers of hydrated sodium ions with channels that hold additional water. At room temperature, Cel-Na($H_2O$)$_x$ exists as a trihydrate between 40-70% RH, a monohydrate from 10-30% RH, and a hemihydrate below 10% RH; PXRD patterns containing both forms are found at humidity close to the transition between two hydration states. The exchange of moisture is rapid and samples must be protected from exposure to air during PXRD measurements to get reproducible patterns. Cel-Na($H_2O$)$_{3-5}$ must be protected from air in order to prevent neutralization of the salt form by carbonic acid formed from carbon dioxide and water. Propylene glycol forms a solvate and a trihydrated solvate of Cel-Na. The Cel-NaPG($H_2O$)$_3$ is physically stable at room temperature above ~10% RH and higher, and the form is resistant to reaction with $CO_2$ and water in the air. Overall, Cel-NaPG($H_2O$)$_3$ is the most shelf-stable form of Cel-Na observed to date and it would be the best choice for use in formulations combining excipients with a salt form to enhance the rate and extent of oral celecoxib absorption.

In accordance with the present invention, crystallization of the hydrated sodium salt of celecoxib with benzyl alcohol enabled structural determination of celecoxib sodium pentahydrate (Cel-Na($H_2O$)$_5$), a structure which proved useful to the understanding of the complex physical behavior of Cel-Na.

The foregoing examples are not intended to limit the scope of the present invention, which is set out in the following claims. In particular, various equivalents and substitutions will be recognized by those skilled in the art in view of the foregoing disclosure and these are contemplated to be within the scope of the invention.

Crystallographic Data

```
# Supplementary Material (ESI) for CrystEngComm

This journal is (c) The Royal Society of Chemistry 2010 data_global

_journal_coden_Cambridge          1350 loop_
_publ_author_name
'Remenar, Julius'
'Tawa, Mark'
'Peterson, Matthew'
'Almarsson, Orn'
'Hickey, Magali'
'Foxman, Bruce'

_publ_contact_author_name         'Remenar, Julius'
_publ_contact_author_email        julius.remenar@alkermes.com _publ_section_title
;
Celecoxib Sodium Salt: Engineering Crystal Forms for Performance
;

Attachment '- Nacelecoxib.cif' data_Nacelecoxib
_database_code_depnum_ccdc_archive 'CCDC 787041'
#TrackingRef '- Nacelecoxib.cif'

_audit_creation_date              09-12-10
_audit_creation_method            CRYSTALS_ver_14.01

_oxford_structure_analysis_title  'p21c_a in P2(1)/c'
_chemical_name_systematic         ?
_chemical_melting_point           ?

_cell_length_a                    25.9317(14)
_cell_length_b                    9.0340(5)
_cell_length_c                    19.4396(10)
_cell_angle_alpha                 90
_cell_angle_beta                  100.535(2)
_cell_angle_gamma                 90
_cell_volume                      4477.3(4)

_symmetry_cell_setting            Monoclinic
_symmetry_space_group_name_H-M    'P 1 21/c 1 '
_symmetry_space_group_name_Hall   ?
loop_
_symmetry_equiv_pos_as_xyz
x,y,z
```

```
-x,-y,-z
-x,y+1/2,-z+1/2
x,-y+1/2,z+1/2 loop_
_atom_type_symbol
_atom_type_scat_dispersion_real
_atom_type_scat_dispersion_imag
_atom_type_scat_Cromer_Mann_a1
_atom_type_scat_Cromer_Mann_b1
_atom_type_scat_Cromer_Mann_a2
_atom_type_scat_Cromer_Mann_b2
_atom_type_scat_Cromer_Mann_a3
_atom_type_scat_Cromer_Mann_b3
_atom_type_scat_Cromer_Mann_a4
_atom_type_scat_Cromer_Mann_b4
_atom_type_scat_Cromer_Mann_c
_atom_type_scat_source
C 0.0033 0.0016 2.3100 20.8439 1.0200 10.2075 1.5886 0.5687 0.8650 51.6512
0.2156 'International Tables Vol C 4.2.6.8 and 6.1.1.4'
H 0.0000 0.0000 0.4930 10.5109 0.3229 26.1257 0.1402 3.1424 0.0408 57.7998
0.0030 'International Tables Vol C 4.2.6.8 and 6.1.1.4'
N 0.0061 0.0033 12.2126 0.0057 3.1322 9.8933 2.0125 28.9975 1.1663 0.5826
-11.5290 'International Tables Vol C 4.2.6.8 and 6.1.1.4'
O 0.0106 0.0060 3.0485 13.2771 2.2868 5.7011 1.5463 0.3239 0.8670 32.9089
0.2508 'International Tables Vol C 4.2.6.8 and 6.1.1.4'
F 0.0171 0.0103 3.5392 10.2825 2.6412 4.2944 1.5170 0.2615 1.0243 26.1476
0.2776 'International Tables Vol C 4.2.6.8 and 6.1.1.4'
Na 0.0362 0.0249 4.7626 3.2850 3.1736 8.8422 1.2674 0.3136 1.1128 129.4240
0.6760 'International Tables Vol C 4.2.6.8 and 6.1.1.4'
S 0.1246 0.1234 6.9053 1.4679 5.2034 22.2151 1.4379 0.2536 1.5863 56.1720
0.8669 'International Tables Vol C 4.2.6.8 and 6.1.1.4'

_cell_formula_units_Z            4

# Given Formula = C34 H46 F6 N6 Na2 O14 S2
# Dc = 1.46 Fooo = 2048.00 Mu = 2.32 M = 986.87
# Found Formula = C34 H46 F6 N6 Na2 O14 S2
# Dc = 1.46 FOOO = 2048.00 Mu = 2.32 M = 986.87

_chemical_formula_sum            'C34 H46 F6 N6 Na2 O14 S2'
_chemical_formula_moiety         'C34 H46 F6 N6 Na2 O14 S2'
_chemical_compound_source        ?
_chemical_formula_weight         986.87

_cell_measurement_reflns_used    9276
_cell_measurement_theta_min      2
_cell_measurement_theta_max      33
_cell_measurement_temperature    100

_exptl_crystal_description       blade
_exptl_crystal_colour            colorless
_exptl_crystal_size_min          0.042
_exptl_crystal_size_mid          0.400
_exptl_crystal_size_max          0.733
```

```
_exptl_crystal_density_diffrn     1.464
_exptl_crystal_density_meas       ?
_exptl_crystal_density_method     'not measured'
# Non-dispersive F(000):
_exptl_crystal_F_000              2048
_exptl_absorpt_coefficient_mu     0.232

# Sheldrick geometric approximatio 0.91 0.99
_exptl_absorpt_correction_type    Multi-scan
_exptl_absorpt_process_details    'Apex2 (Bruker AXS, 2006)'
_exptl_absorpt_correction_T_min   0.91
_exptl_absorpt_correction_T_max   0.99
_diffrn_measurement_device-type   'Bruker Kappa Apex2'
_diffrn_measurement_device        Area
_diffrn_radiation_monochromator   graphite
_diffrn_radiation_type            'Mo K\a'
_diffrn_radiation_wavelength      0.71073
_diffrn_measurement_method        '\f & \w scans'

# If a reference occurs more than once, delete the author
# and date from subsequent references.
_computing_data_collection        'Apex2 (Bruker AXS, 2006)'
_computing_cell_refinement        'Apex2 (Bruker AXS, 2006)'
_computing_data_reduction         'Apex2 (Bruker AXS, 2006)'
_computing_structure_solution     'SIR92 (Altomare et al., 1994)'
_computing_structure_refinement   'CRYSTALS (Betteridge et al., 2003)'
_computing_publication_material   'CRYSTALS (Betteridge et al., 2003)'
_computing_molecular_graphics     'CAMERON (Watkin et al., 1996)'

_diffrn_standards_interval_time   .
_diffrn_standards_interval_count  .
_diffrn_standards_number          0
_diffrn_standards_decay_%         ?

_diffrn_ambient_temperature       100
_diffrn_reflns_number             80228
_reflns_number_total              17648
_diffrn_reflns_av_R_equivalents   0.029
# Number of reflections without Friedels Law is 17648
# Number of reflections with Friedels Law is 0
# Theoretical number of reflections is about 17707

_diffrn_reflns_theta_min          2.392
_diffrn_reflns_theta_max          33.601
_diffrn_measured_fraction_theta_max 0.997

_diffrn_reflns_theta_full         33.601
_diffrn_measured_fraction_theta_full 0.997

_diffrn_reflns_limit_h_min        -40
_diffrn_reflns_limit_h_max        40
_diffrn_reflns_limit_k_min        -12
_diffrn_reflns_limit_k_max        14
_diffrn_reflns_limit_l_min        -20
```

```
_diffrn_reflns_limit_l_max        30
_reflns_limit_h_min               -40
_reflns_limit_h_max               39
_reflns_limit_k_min               0
_reflns_limit_k_max               14
_reflns_limit_l_min               0
_reflns_limit_l_max               30

_oxford_diffrn_Wilson_B_factor    1.17
_oxford_diffrn_Wilson_scale       12.35

_atom_sites_solution_primary      direct #heavy,direct,difmap,geom
# _atom_sites_solution_secondary  difmap
_atom_sites_solution_hydrogens    geom _refine_diff_density_min          -0.71
_refine_diff_density_max          0.96

# The current dictionary definitions do not cover the
# situation where the reflections used for refinement were
# selected by a user-defined sigma threshold

# The values actually used during refinement
_oxford_reflns_threshold_expression_ref I>-10.0\s(I)
_refine_ls_number_reflns          17621
_refine_ls_number_restraints      0
_refine_ls_number_parameters      580
_oxford_refine_ls_R_factor_ref    0.0623
_refine_ls_wR_factor_ref          0.1163
_refine_ls_goodness_of_fit_ref    0.9840
_refine_ls_shift/su_max           0.0010532
_refine_ls_shift/su_mean          0.0000664

# The values computed from all data
_oxford_reflns_number_all         17621
_refine_ls_R_factor_all           0.0623
_refine_ls_wR_factor_all          0.1163

# The values computed with a 2 sigma cutoff - a la SHELX
_reflns_threshold_expression      I>2.0\s(I)
_reflns_number_gt                 13607
_refine_ls_R_factor_gt            0.0431
_refine_ls_wR_factor_gt           0.1065 choose from: rm (reference molecule of known chirality),
ad (anomalous dispersion - Flack), rmad (rm and ad),
# syn (from synthesis), unk (unknown) or . (not applicable).
_chemical_absolute_configuration  .

_refine_ls_structure_factor_coef  Fsqd
_refine_ls_matrix_type            full
_refine_ls_hydrogen_treatment     none # none, undef, noref, refall,
# refxyz, refU, constr or mixed
_refine_ls_weighting_scheme       calc
_refine_ls_weighting_details
```

```
;
Method= Modified Sheldrick
w=1/[\s^2^(F^2^) + ( 0.05P)^2^ + 3.09P]
,where P=(max(Fo^2^,0) + 2Fc^2^)/3
;
# Insert your own references if required - in alphabetical order
_publ_section_references
;
Altomare, A., Cascarano, G., Giacovazzo, C., Guagliardi, A., Burla, M.C.,
Polidori, G. & Camalli, M. (1994). J. Appl. Cryst. 27, 435.

Betteridge, P.W., Carruthers, J.R., Cooper, R.I.,
Prout, K. & Watkin, D.J. (2003). J. Appl. Cryst. 36, 1487.

Bruker Analytical X-ray Systems, Inc., 2006. <i>Apex2</i>,
Version 2 User Manual, M86-E01078, Madison, WI.

Watkin, D.J., Prout, C.K. & Pearce, L.J. (1996). CAMERON, Chemical
Crystallography Laboratory, Oxford, UK.
;

Uequiv = arithmetic mean of Ui i.e. Ueqiv = (U1+U2+U3)/3

Replace last . with number of unfound hydrogen atomsattached to an atom.

# ..._refinement_flags_...
# . no refinement constraints S special position constraint on site
# G rigid group refinement of site R riding atom
# D distance or angle restraint on site T thermal displacement constraints
U Uiso or Uij restraint (rigid bond) P partial occupancy constraint loop_
_atom_site_label
_atom_site_type_symbol
_atom_site_fract_x
_atom_site_fract_y
_atom_site_fract_z
_atom_site_U_iso_or_equiv
_atom_site_occupancy
_atom_site_adp_type
_atom_site_refinement_flags_posn
_atom_site_refinement_flags_adp
_atom_site_refinement_flags_occupancy
_atom_site_disorder_assembly
_atom_site_disorder_group
_oxford_atom_site_special_shape
_atom_site_attached_hydrogens
S1   S  0.123342(10)  0.27593(3)   0.314579(14) 0.0116 1.0000 Uani . . . . . . . .
S101 S  0.129795(11)  0.75560(3)   0.224947(16) 0.0146 1.0000 Uani . . . . . . . .
Na1  Na 0.033913(19)  0.45734(6)   0.17876(3)   0.0152 1.0000 Uani . . . . . . . .
Na2  Na 0.0000        0.0000       0.0000       0.0205 1.0000 Uani S . . . . . . .
Na3  Na 0.0000        0.5000       0.0000       0.0256 1.0000 Uani S . . . . . . .
F1   F  0.35361(4)   -0.00402(14) -0.03748(5)   0.0391 1.0000 Uani . . . . . . . .
F2   F  0.28658(6)    0.13817(16) -0.06348(5)   0.0554 1.0000 Uani . . . . . . . .
F3   F  0.27659(5)   -0.08895(16) -0.03832(6)   0.0512 1.0000 Uani . . . . . . . .
```

```
F101  F   0.46324(5)   0.6126(2)    0.42846(6)   0.0660 1.0000 Uani
F102  F   0.51497(5)   0.72473(15)  0.37110(8)   0.0585 1.0000 Uani
F103  F   0.50858(4)   0.49111(13)  0.36704(6)   0.0413 1.0000 Uani
O1    O   0.12555(4)   0.15103(11)  0.36287(5)   0.0174 1.0000 Uani
O2    O   0.07631(3)   0.27729(10)  0.25975(5)   0.0154 1.0000 Uani
O3    O  -0.03086(4)   0.27649(12)  0.14172(6)   0.0277 1.0000 Uani
O4    O   0.07088(4)   0.39014(11)  0.07728(5)   0.0183 1.0000 Uani
O5    O  -0.02269(3)   0.50734(10)  0.26325(5)   0.0173 1.0000 Uani
O6    O  -0.02351(4)   0.61452(11)  0.10013(5)   0.0181 1.0000 Uani
O7    O  -0.05315(5)   0.25595(14) -0.01909(7)   0.0332 1.0000 Uani
O8    O   0.02870(4)   0.05517(12) -0.10365(5)   0.0227 1.0000 Uani
O9    O   0.08086(4)   0.08322(11)  0.06909(5)   0.0205 1.0000 Uani
O10   O   0.15793(5)   0.44933(13)  0.00995(6)   0.0289 1.0000 Uani
O11   O   0.16390(4)   0.03678(13) -0.00038(5)   0.0250 1.0000 Uani
O12   O   0.14857(6)  -0.26278(15) -0.04751(7)   0.0406 1.0000 Uani
O101  O   0.10536(3)   0.61027(10)  0.22142(5)   0.0190 1.0000 Uani
O102  O   0.11394(4)   0.84392(13)  0.16195(6)   0.0269 1.0000 Uani
N1    N   0.13193(4)   0.42092(12)  0.35713(5)   0.0162 1.0000 Uani
N2    N   0.27023(4)   0.11199(13)  0.07796(5)   0.0177 1.0000 Uani
N3    N   0.28806(4)   0.13792(12)  0.14700(5)   0.0148 1.0000 Uani
N101  N   0.12138(4)   0.82890(14)  0.29429(7)   0.0214 1.0000 Uani
N102  N   0.38864(4)   0.65110(14)  0.31500(6)   0.0200 1.0000 Uani
N103  N   0.36028(4)   0.64810(13)  0.24890(6)   0.0168 1.0000 Uani
C1    C   0.17493(4)   0.24286(13)  0.26736(6)   0.0125 1.0000 Uani
C2    C   0.17416(5)   0.31402(14)  0.20364(6)   0.0155 1.0000 Uani
C3    C   0.21245(5)   0.28176(15)  0.16428(6)   0.0157 1.0000 Uani
C4    C   0.25061(4)   0.17737(14)  0.18944(6)   0.0138 1.0000 Uani
C5    C   0.25188(5)   0.10690(15)  0.25302(6)   0.0162 1.0000 Uani
C6    C   0.21406(5)   0.14146(15)  0.29277(6)   0.0156 1.0000 Uani
C7    C   0.31264(5)   0.06863(16)  0.05393(7)   0.0194 1.0000 Uani
C8    C   0.35768(5)   0.06565(17)  0.10586(7)   0.0206 1.0000 Uani
C9    C   0.34080(5)   0.11132(15)  0.16587(6)   0.0161 1.0000 Uani
C10   C   0.30721(6)   0.0294(2)   -0.02126(7)   0.0290 1.0000 Uani
C11   C   0.37093(5)   0.13234(15)  0.23688(6)   0.0167 1.0000 Uani
C12   C   0.40684(5)   0.02442(16)  0.26624(7)   0.0212 1.0000 Uani
C13   C   0.43484(5)   0.04178(18)  0.33400(8)   0.0252 1.0000 Uani
C14   C   0.42793(5)   0.16485(19)  0.37385(7)   0.0250 1.0000 Uani
C15   C   0.39292(6)   0.27400(18)  0.34368(7)   0.0249 1.0000 Uani
C16   C   0.36477(5)   0.25840(16)  0.27613(7)   0.0213 1.0000 Uani
C17   C   0.45621(7)   0.1811(3)    0.44858(9)   0.0393 1.0000 Uani
C101  C   0.19830(5)   0.72328(14)  0.22939(6)   0.0150 1.0000 Uani
C102  C   0.22449(5)   0.77850(15)  0.17856(7)   0.0186 1.0000 Uani
C103  C   0.27837(5)   0.75537(15)  0.18442(7)   0.0189 1.0000 Uani
C104  C   0.30492(4)   0.67356(14)  0.24031(6)   0.0152 1.0000 Uani
C105  C   0.27874(5)   0.61616(16)  0.29061(7)   0.0189 1.0000 Uani
C106  C   0.22539(5)   0.64214(16)  0.28552(7)   0.0188 1.0000 Uani
C107  C   0.43742(5)   0.62539(18)  0.30630(7)   0.0239 1.0000 Uani
C108  C   0.44160(5)   0.60621(19)  0.23616(8)   0.0261 1.0000 Uani
C109  C   0.39088(5)   0.61960(16)  0.19989(7)   0.0195 1.0000 Uani
C110  C   0.48072(6)   0.6151(2)    0.36835(9)   0.0315 1.0000 Uani
C111  C   0.37114(5)   0.60055(16)  0.12466(7)   0.0192 1.0000 Uani
C112  C   0.32778(5)   0.51143(17)  0.09970(7)   0.0222 1.0000 Uani
C113  C   0.31005(6)   0.49608(18)  0.02850(7)   0.0245 1.0000 Uani
C114  C   0.33545(6)   0.56764(17) -0.01941(7)   0.0232 1.0000 Uani
C115  C   0.37950(6)   0.65294(19)  0.00560(8)   0.0267 1.0000 Uani
```

```
C116  C  0.39721(5)  0.66954(18)  0.07712(8)   0.0247  1.0000  Uani ........
C117  C  0.31507(7)  0.5539(2)   -0.09675(8)   0.0321  1.0000  Uani ........
H11   H  0.1277      0.4963       0.3315       0.0201  1.0000  Uiso R ......
H21   H  0.1475      0.3835       0.1870       0.0189  1.0000  Uiso R ......
H31   H  0.2106      0.3298       0.1207       0.0204  1.0000  Uiso R ......
H32   H -0.0544      0.2819       0.1603       0.0401  1.0000  Uiso R ......
H33   H -0.0318      0.1890       0.1313       0.0435  1.0000  Uiso R ......
H41   H  0.0737      0.3004       0.0762       0.0280  1.0000  Uiso R ......
H42   H  0.0959      0.4173       0.0630       0.0271  1.0000  Uiso R ......
H51   H  0.2776      0.0365       0.2686       0.0199  1.0000  Uiso R ......
H52   H -0.0346      0.5908       0.2603       0.0259  1.0000  Uiso R ......
H53   H -0.0477      0.4531       0.2513       0.0268  1.0000  Uiso R ......
H61   H  0.2134      0.0977       0.3360       0.0185  1.0000  Uiso R ......
H62   H -0.0528      0.6055       0.1086       0.0285  1.0000  Uiso R ......
H63   H -0.0192      0.7042       0.0978       0.0272  1.0000  Uiso R ......
H71   H -0.0329      0.2583       0.0161       0.0479  1.0000  Uiso R ......
H72   H -0.0775      0.2601       0.0046       0.0507  1.0000  Uiso R ......
H81   H  0.3917      0.0423       0.1004       0.0253  1.0000  Uiso R ......
H82   H  0.0100      0.0479      -0.1428       0.0345  1.0000  Uiso R ......
H83   H  0.0593      0.0628      -0.1090       0.0342  1.0000  Uiso R ......
H91   H  0.1061      0.0714       0.0499       0.0323  1.0000  Uiso R ......
H92   H  0.0899      0.0322       0.1039       0.0310  1.0000  Uiso R ......
H101  H  0.1599      0.5358      -0.0022       0.0435  1.0000  Uiso R ......
H102  H  0.1520      0.3998      -0.0246       0.0452  1.0000  Uiso R ......
H111  H  0.1929      0.0625       0.0167       0.0376  1.0000  Uiso R ......
H112  H  0.1617      0.0589      -0.0402       0.0376  1.0000  Uiso R ......
H121  H  0.4112     -0.0615       0.2401       0.0243  1.0000  Uiso R ......
H122  H  0.1527     -0.2682      -0.0912       0.0621  1.0000  Uiso R ......
H123  H  0.1610     -0.1751      -0.0333       0.0607  1.0000  Uiso R ......
H131  H  0.4586     -0.0305       0.3524       0.0308  1.0000  Uiso R ......
H151  H  0.3875      0.3591       0.3681       0.0304  1.0000  Uiso R ......
H161  H  0.3411      0.3326       0.2569       0.0260  1.0000  Uiso R ......
H171  H  0.4347      0.1566       0.4804       0.0596  1.0000  Uiso R ......
H172  H  0.4687      0.2777       0.4570       0.0599  1.0000  Uiso R ......
H173  H  0.4862      0.1183       0.4564       0.0600  1.0000  Uiso R ......
H1011 H  0.1334      0.9161       0.2975       0.0267  1.0000  Uiso R ......
H1021 H  0.2068      0.8352       0.1411       0.0224  1.0000  Uiso R ......
H1031 H  0.2964      0.7948       0.1505       0.0243  1.0000  Uiso R ......
H1051 H  0.2984      0.5614       0.3270       0.0233  1.0000  Uiso R ......
H1061 H  0.2076      0.6051       0.3208       0.0240  1.0000  Uiso R ......
H1081 H  0.4712      0.5851       0.2178       0.0314  1.0000  Uiso R ......
H1121 H  0.3096      0.4608       0.1329       0.0271  1.0000  Uiso R ......
H1131 H  0.2811      0.4354       0.0136       0.0306  1.0000  Uiso R ......
H1151 H  0.3973      0.7021      -0.0257       0.0324  1.0000  Uiso R ......
H1161 H  0.4258      0.7305       0.0933       0.0300  1.0000  Uiso R ......
H1171 H  0.3355      0.6043      -0.1239       0.0477  1.0000  Uiso R ......
H1172 H  0.2814      0.5956      -0.1072       0.0472  1.0000  Uiso R ......
H1173 H  0.3121      0.4526      -0.1115       0.0477  1.0000  Uiso R ......
loop_
_atom_site_aniso_label
_atom_site_aniso_U_11
_atom_site_aniso_U_22
_atom_site_aniso_U_33
_atom_site_aniso_U_23
_atom_site_aniso_U_13
```

```
_atom_site_aniso_U_12
S1    0.01014(10) 0.01360(12) 0.01149(11) 0.00079(9)  0.00331(8)  0.00035(9)
S101  0.01143(11) 0.01309(12) 0.01967(13) 0.00163(10) 0.00383(9)  0.00091(9)
Na1   0.0136(2)   0.0168(2)   0.0151(2)   0.00084(18) 0.00205(16) 0.00004(17)
Na2   0.0194(3)   0.0296(4)   0.0132(3)   0.0013(3)   0.0051(3)   -0.0052(3)
Na3   0.0264(4)   0.0322(4)   0.0159(3)   -0.0055(3)  -0.0027(3)  0.0140(3)
F1    0.0374(5)   0.0603(7)   0.0250(4)   -0.0056(5)  0.0198(4)   0.0084(5)
F2    0.0785(9)   0.0704(9)   0.0167(4)   0.0045(5)   0.0073(5)   0.0368(7)
F3    0.0508(7)   0.0732(9)   0.0318(5)   -0.0293(6)  0.0135(5)   -0.0201(6)
F101  0.0309(5)   0.1399(15)  0.0232(5)   -0.0169(7)  -0.0055(4)  0.0219(7)
F102  0.0333(6)   0.0455(7)   0.0821(10)  -0.0065(7)  -0.0279(6)  -0.0065(5)
F103  0.0268(5)   0.0459(6)   0.0459(6)   -0.0011(5)  -0.0074(4)  0.0102(4)
O1    0.0174(4)   0.0184(4)   0.0176(4)   0.0059(3)   0.0066(3)   0.0024(3)
O2    0.0113(3)   0.0175(4)   0.0165(4)   0.0008(3)   0.0000(3)   -0.0008(3)
O3    0.0251(5)   0.0223(5)   0.0372(6)   -0.0097(4)  0.0100(4)   -0.0025(4)
O4    0.0183(4)   0.0178(4)   0.0190(4)   0.0004(3)   0.0036(3)   0.0026(3)
O5    0.0157(4)   0.0158(4)   0.0202(4)   -0.0001(3)  0.0027(3)   0.0003(3)
O6    0.0177(4)   0.0175(4)   0.0204(4)   0.0015(3)   0.0075(3)   0.0027(3)
O7    0.0378(6)   0.0329(6)   0.0325(6)   0.0018(5)   0.0155(5)   -0.0020(5)
O8    0.0184(4)   0.0360(6)   0.0147(4)   0.0014(4)   0.0062(3)   -0.0052(4)
O9    0.0206(4)   0.0204(4)   0.0201(4)   0.0033(4)   0.0029(3)   0.0019(3)
O10   0.0348(6)   0.0283(6)   0.0235(5)   0.0021(4)   0.0050(4)   -0.0025(4)
O11   0.0201(4)   0.0375(6)   0.0167(4)   0.0022(4)   0.0016(3)   -0.0040(4)
O12   0.0548(8)   0.0328(7)   0.0329(6)   0.0039(5)   0.0041(6)   -0.0104(6)
O101  0.0146(4)   0.0144(4)   0.0275(5)   -0.0020(3)  0.0027(3)   -0.0021(3)
O102  0.0212(4)   0.0298(5)   0.0303(5)   0.0143(4)   0.0061(4)   0.0078(4)
N1    0.0182(4)   0.0169(5)   0.0145(4)   -0.0026(4)  0.0053(3)   -0.0006(4)
N2    0.0169(4)   0.0258(5)   0.0104(4)   -0.0027(4)  0.0027(3)   0.0010(4)
N3    0.0123(4)   0.0212(5)   0.0112(4)   -0.0021(4)  0.0030(3)   0.0021(3)
N101  0.0179(5)   0.0193(5)   0.0288(6)   -0.0075(4)  0.0091(4)   -0.0011(4)
N102  0.0134(4)   0.0282(6)   0.0175(5)   -0.0043(4)  0.0002(4)   0.0007(4)
N103  0.0109(4)   0.0238(5)   0.0156(4)   -0.0028(4)  0.0021(3)   -0.0003(4)
C1    0.0112(4)   0.0151(5)   0.0117(4)   -0.0012(4)  0.0029(3)   0.0012(4)
C2    0.0146(5)   0.0182(5)   0.0141(5)   0.0021(4)   0.0040(4)   0.0038(4)
C3    0.0153(5)   0.0203(5)   0.0123(4)   0.0023(4)   0.0042(4)   0.0033(4)
C4    0.0124(4)   0.0184(5)   0.0113(4)   -0.0018(4)  0.0035(3)   0.0016(4)
C5    0.0144(5)   0.0213(6)   0.0132(5)   0.0016(4)   0.0030(4)   0.0057(4)
C6    0.0144(5)   0.0206(6)   0.0121(4)   0.0031(4)   0.0033(4)   0.0043(4)
C7    0.0187(5)   0.0271(6)   0.0138(5)   -0.0029(5)  0.0066(4)   0.0012(5)
C8    0.0152(5)   0.0294(7)   0.0188(5)   -0.0036(5)  0.0069(4)   0.0018(5)
C9    0.0122(4)   0.0214(6)   0.0150(5)   -0.0019(4)  0.0031(4)   0.0009(4)
C10   0.0300(7)   0.0426(9)   0.0162(6)   -0.0052(6)  0.0088(5)   0.0057(6)
C11   0.0126(5)   0.0219(6)   0.0155(5)   -0.0020(4)  0.0023(4)   -0.0007(4)
C12   0.0161(5)   0.0239(6)   0.0230(6)   -0.0007(5)  0.0021(4)   0.0024(4)
C13   0.0183(6)   0.0306(7)   0.0247(6)   0.0050(6)   -0.0016(5)  0.0016(5)
C14   0.0205(6)   0.0350(8)   0.0178(5)   0.0011(5)   -0.0010(4)  -0.0070(5)
C15   0.0262(6)   0.0274(7)   0.0200(6)   -0.0065(5)  0.0011(5)   -0.0042(5)
C16   0.0213(6)   0.0222(6)   0.0192(5)   -0.0031(5)  0.0002(4)   0.0010(5)
C17   0.0369(9)   0.0555(12)  0.0210(7)   0.0021(7)   -0.0066(6)  -0.0098(8)
C101  0.0133(4)   0.0143(5)   0.0177(5)   0.0001(4)   0.0039(4)   -0.0004(4)
C102  0.0150(5)   0.0209(6)   0.0207(5)   0.0055(5)   0.0055(4)   0.0021(4)
C103  0.0147(5)   0.0213(6)   0.0220(6)   0.0040(5)   0.0068(4)   0.0000(4)
C104  0.0106(4)   0.0186(5)   0.0166(5)   -0.0023(4)  0.0028(4)   -0.0010(4)
C105  0.0133(5)   0.0282(7)   0.0151(5)   0.0034(5)   0.0023(4)   0.0015(4)
C106  0.0131(5)   0.0268(6)   0.0171(5)   0.0040(5)   0.0042(4)   0.0003(4)
```

```
C107   0.0129(5)  0.0344(7)   0.0233(6)  -0.0072(6)   0.0003(4)   0.0017(5)
C108   0.0133(5)  0.0400(8)   0.0251(6)  -0.0084(6)   0.0041(5)   0.0014(5)
C109   0.0132(5)  0.0269(6)   0.0190(5)  -0.0054(5)   0.0046(4)  -0.0014(4)
C110   0.0169(6)  0.0464(10)  0.0288(7)  -0.0111(7)  -0.0026(5)   0.0051(6)
C111   0.0153(5)  0.0246(6)   0.0184(5)  -0.0045(5)   0.0051(4)  -0.0014(4)
C112   0.0214(6)  0.0255(7)   0.0202(6)  -0.0017(5)   0.0049(4)  -0.0060(5)
C113   0.0231(6)  0.0283(7)   0.0214(6)  -0.0043(5)   0.0023(5)  -0.0069(5)
C114   0.0233(6)  0.0273(7)   0.0187(6)  -0.0024(5)   0.0032(5)   0.0011(5)
C115   0.0263(6)  0.0340(8)   0.0222(6)  -0.0015(6)   0.0104(5)  -0.0058(6)
C116   0.0196(6)  0.0326(7)   0.0238(6)  -0.0064(6)   0.0089(5)  -0.0084(5)
C117   0.0330(8)  0.0433(9)   0.0187(6)  -0.0010(6)   0.0012(5)   0.0004(7)

_refine_ls_extinction_method         None
_oxford_refine_ls_scale              0.31558(18)
loop_
_geom_bond_atom_site_label_1
_geom_bond_site_symmetry_1
_geom_bond_atom_site_label_2
_geom_bond_site_symmetry_2
_geom_bond_distance
_geom_bond_publ_flag
S1   . O1   . 1.4622(9)  yes
S1   . O2   . 1.4657(9)  yes
S1   . N1   . 1.5435(11) yes
S1   . C1   . 1.7806(11) yes
S101 . O101 . 1.4540(10) yes
S101 . O102 . 1.4565(11) yes
S101 . N101 . 1.5527(12) yes
S101 . C101 . 1.7868(12) yes
Na1  . O2   . 2.3875(10) yes
Na1  . O3   . 2.3594(12) yes
Na1  . O4   . 2.4229(11) yes
Na1  . O5   . 2.4366(10) yes
Na1  . O6   . 2.3954(11) yes
Na1  . O101 . 2.3382(10) yes
Na2  . O8   2_555 2.3260(9)  yes
Na2  . O9   2_555 2.3949(10) yes
Na2  . O7   2_555 2.6826(13) yes
Na2  . O7   . 2.6826(13) yes
Na2  . O8   . 2.3260(9)  yes
Na2  . O9   . 2.3949(10) yes
Na3  . O4   2_565 2.3687(9)  yes
Na3  . O6   2_565 2.3800(9)  yes
Na3  . O7   2_565 2.5906(13) yes
Na3  . O4   . 2.3687(9)  yes
Na3  . O6   . 2.3800(9)  yes
Na3  . O7   . 2.5906(13) yes
F1   . C10  . 1.3330(17) yes
F2   . C10  . 1.328(2)   yes
F3   . C10  . 1.337(2)   yes
F101 . C110 . 1.328(2)   yes
F102 . C110 . 1.325(2)   yes
F103 . C110 . 1.335(2)   yes
O3   . H32  . 0.766      no
O3   . H33  . 0.815      no
```

```
O4   . H41   . 0.815     no
O4   . H42   . 0.791     no
O5   . H52   . 0.812     no
O5   . H53   . 0.813     no
O6   . H62   . 0.810     no
O6   . H63   . 0.821     no
O7   . H71   . 0.783     no
O7   . H72   . 0.849     no
O8   . H82   . 0.828     no
O8   . H83   . 0.823     no
O9   . H91   . 0.818     no
O9   . H92   . 0.817     no
O10  . H101  . 0.820     no
O10  . H102  . 0.798     no
O11  . H111  . 0.800     no
O11  . H112  . 0.791     no
O12  . H122  . 0.877     no
O12  . H123  . 0.881     no
N1   . H11   . 0.840     no
N2   . N3    . 1.3576(14) yes
N2   . C7    . 1.3299(16) yes
N3   . C4    . 1.4295(15) yes
N3   . C9    . 1.3709(15) yes
N101 . H1011 . 0.846     no
N102 . N103  . 1.3593(15) yes
N102 . C107  . 1.3271(17) yes
N103 . C104  . 1.4329(15) yes
N103 . C109  . 1.3713(16) yes
C1   . C2    . 1.3926(16) yes
C1   . C6    . 1.3890(16) yes
C2   . C3    . 1.3905(16) yes
C2   . H21   . 0.947     no
C3   . C4    . 1.3896(17) yes
C3   . H31   . 0.945     no
C4   . C5    . 1.3853(16) yes
C5   . C6    . 1.3905(16) yes
C5   . H51   . 0.932     no
C6   . H61   . 0.932     no
C7   . C8    . 1.3973(18) yes
C7   . C10   . 1.4854(19) yes
C8   . C9    . 1.3817(17) yes
C8   . H81   . 0.932     no
C9   . C11   . 1.4690(17) yes
C11  . C12   . 1.3961(18) yes
C11  . C16   . 1.3961(19) yes
C12  . C13   . 1.3918(19) yes
C12  . H121  . 0.946     no
C13  . C14   . 1.385(2)  yes
C13  . H131  . 0.924     no
C14  . C15   . 1.395(2)  yes
C14  . C17   . 1.510(2)  yes
C15  . C16   . 1.3880(19) yes
C15  . H151  . 0.928     no
C16  . H161  . 0.939     no
C17  . H171  . 0.932     no
```

```
C17  . H172  . 0.935     no
C17  . H173  . 0.953     no
C101 . C102  . 1.3900(17) yes
C101 . C106  . 1.3932(17) yes
C102 . C103  . 1.3965(17) yes
C102 . H1021 . 0.939     no
C103 . C104  . 1.3883(18) yes
C103 . H1031 . 0.944     no
C104 . C105  . 1.3888(17) yes
C105 . C106  . 1.3889(17) yes
C105 . H1051 . 0.935     no
C106 . H1061 . 0.954     no
C107 . C108  . 1.398(2)  yes
C107 . C110  . 1.493(2)  yes
C108 . C109  . 1.3792(18) yes
C108 . H1081 . 0.924     no
C109 . C111  . 1.4686(18) yes
C111 . C112  . 1.3959(18) yes
C111 . C116  . 1.3886(19) yes
C112 . C113  . 1.3834(19) yes
C112 . H1121 . 0.979     no
C113 . C114  . 1.394(2)  yes
C113 . H1131 . 0.933     no
C114 . C115  . 1.390(2)  yes
C114 . C117  . 1.505(2)  yes
C115 . C116  . 1.390(2)  yes
C115 . H1151 . 0.940     no
C116 . H1161 . 0.930     no
C117 . H1171 . 0.933     no
C117 . H1172 . 0.937     no
C117 . H1173 . 0.958     no
loop_
_geom_angle_atom_site_label_1
_geom_angle_site_symmetry_1
_geom_angle_atom_site_label_2
_geom_angle_site_symmetry_2
_geom_angle_atom_site_label_3
_geom_angle_site_symmetry_3
_geom_angle
_geom_angle_publ_flag
O1   . S1   . O2   . 113.77(5) yes
O1   . S1   . N1   . 109.02(6) yes
O2   . S1   . N1   . 113.70(6) yes
O1   . S1   . C1   . 104.87(5) yes
O2   . S1   . C1   . 103.31(5) yes
N1   . S1   . C1   . 111.73(6) yes
O101 . S101 . O102 . 113.67(6) yes
O101 . S101 . N101 . 107.27(6) yes
O102 . S101 . N101 . 115.69(7) yes
O101 . S101 . C101 . 106.00(6) yes
O102 . S101 . C101 . 104.80(6) yes
N101 . S101 . C101 . 108.90(6) yes
O2   . Na1  . O3   . 86.89(4)  yes
O2   . Na1  . O4   . 99.39(4)  yes
O3   . Na1  . O4   . 86.77(4)  yes
```

```
O2  .     Na1 . O5  .   86.75(3)  yes
O3  .     Na1 . O5  .   81.44(4)  yes
O4  .     Na1 . O5  .  166.41(4)  yes
O2  .     Na1 . O6  .  169.19(4)  yes
O3  .     Na1 . O6  .   83.74(4)  yes
O4  .     Na1 . O6  .   85.48(3)  yes
O5  .     Na1 . O6  .   86.53(3)  yes
O2  .     Na1 . O101 .  85.94(4)  yes
O3  .     Na1 . O101 . 172.35(4)  yes
O4  .     Na1 . O101 .  91.78(4)  yes
O5  .     Na1 . O101 . 100.80(4)  yes
O6  .     Na1 . O101 . 103.64(4)  yes
O8  2_555 Na2 . O9  2_555  91.87(3)  yes
O8  2_555 Na2 . O7  2_555  86.16(4)  yes
O9  2_555 Na2 . O7  2_555 100.49(4)  yes
O8  2_555 Na2 . O7  .  93.84(4)  yes
O9  2_555 Na2 . O7  .  79.51(4)  yes
O7  2_555 Na2 . O7  . 179.996    yes
O8  2_555 Na2 . O8  . 179.995    yes
O9  2_555 Na2 . O8  .  88.13(3)  yes
O7  2_555 Na2 . O8  .  93.84(4)  yes
O7  .     Na2 . O8  .  86.16(4)  yes
O8  2_555 Na2 . O9  .  88.13(3)  yes
O9  2_555 Na2 . O9  . 179.995    yes
O7  2_555 Na2 . O9  .  79.51(4)  yes
O7  .     Na2 . O9  . 100.49(4)  yes
O8  .     Na2 . O9  .  91.87(3)  yes
O4  2_565 Na3 . O6  2_565  87.05(3)  yes
O4  2_565 Na3 . O7  2_565  93.73(4)  yes
O6  2_565 Na3 . O7  2_565 106.14(4)  yes
O4  2_565 Na3 . O4  . 179.995    yes
O6  2_565 Na3 . O4  .  92.95(3)  yes
O7  2_565 Na3 . O4  .  86.27(4)  yes
O4  2_565 Na3 . O6  .  92.95(3)  yes
O6  2_565 Na3 . O6  . 179.995    yes
O7  2_565 Na3 . O6  .  73.86(4)  yes
O4  .     Na3 . O6  .  87.05(3)  yes
O4  2_565 Na3 . O7  .  86.27(4)  yes
O6  2_565 Na3 . O7  .  73.86(4)  yes
O7  2_565 Na3 . O7  . 179.996    yes
O4  .     Na3 . O7  .  93.73(4)  yes
O6  .     Na3 . O7  . 106.14(4)  yes
Na1 .     O2  . S1  . 134.98(6)  yes
Na1 .     O3  . H32 . 113.3      no
Na1 .     O3  . H33 . 137.3      no
H32 .     O3  . H33 . 100.9      no
Na3 .     O4  . Na1 .  91.99(3)  yes
Na3 .     O4  . H41 . 117.6      no
Na1 .     O4  . H41 . 108.7      no
Na3 .     O4  . H42 . 103.9      no
Na1 .     O4  . H42 . 132.9      no
H41 .     O4  . H42 . 102.5      no
Na1 .     O5  . H52 . 113.1      no
Na1 .     O5  . H53 . 104.1      no
H52 .     O5  . H53 . 105.4      no
```

```
Na3 . O6  . Na1  .  92.40(3)   yes
Na3 . O6  . H62  . 120.8       no
Na1 . O6  . H62  . 107.9       no
Na3 . O6  . H63  . 109.1       no
Na1 . O6  . H63  . 123.1       no
H62 . O6  . H63  . 104.6       no
Na3 . O7  . Na2  . 117.86(5)   yes
Na3 . O7  . H71  .  66.2       no
Na2 . O7  . H71  .  69.9       no
Na3 . O7  . H72  . 108.3       no
Na2 . O7  . H72  . 112.2       no
H71 . O7  . H72  .  88.5       no
Na2 . O8  . H82  . 123.7       no
Na2 . O8  . H83  . 126.7       no
H82 . O8  . H83  . 107.9       no
Na2 . O9  . H91  . 113.2       no
Na2 . O9  . H92  . 112.1       no
H91 . O9  . H92  . 100.0       no
H101 . O10 . H102 . 107.7      no
H111 . O11 . H112 . 103.1      no
H122 . O12 . H123 . 104.6      no
Na1 . O101 . S101 . 149.38(6)  yes
S1  . N1  . H11  . 112.3       no
N3  . N2  . C7   . 104.12(10)  yes
N2  . N3  . C4   . 117.98(9)   yes
N2  . N3  . C9   . 112.14(10)  yes
C4  . N3  . C9   . 129.72(10)  yes
S101 . N101 . H1011 . 110.7    no
N103 . N102 . C107 . 103.87(11) yes
N102 . N103 . C104 . 117.67(10) yes
N102 . N103 . C109 . 112.25(10) yes
C104 . N103 . C109 . 130.08(10) yes
S1  . C1  . C2   . 119.42(9)   yes
S1  . C1  . C6   . 119.75(9)   yes
C2  . C1  . C6   . 120.76(10)  yes
C1  . C2  . C3   . 119.81(11)  yes
C1  . C2  . H21  . 120.0       no
C3  . C2  . H21  . 120.2       no
C2  . C3  . C4   . 118.87(11)  yes
C2  . C3  . H31  . 118.2       no
C4  . C3  . H31  . 122.9       no
N3  . C4  . C3   . 118.77(10)  yes
N3  . C4  . C5   . 119.51(10)  yes
C3  . C4  . C5   . 121.67(11)  yes
C4  . C5  . C6   . 119.25(11)  yes
C4  . C5  . H51  . 120.2       no
C6  . C5  . H51  . 120.6       no
C5  . C6  . C1   . 119.61(11)  yes
C5  . C6  . H61  . 122.5       no
C1  . C6  . H61  . 117.9       no
N2  . C7  . C8   . 112.81(11)  yes
N2  . C7  . C10  . 118.69(12)  yes
C8  . C7  . C10  . 128.50(12)  yes
C7  . C8  . C9   . 104.61(11)  yes
C7  . C8  . H81  . 127.3       no
```

```
C9  . C8  . H81 . 128.0     no
C8  . C9  . N3  . 106.32(10) yes
C8  . C9  . C11 . 129.49(11) yes
N3  . C9  . C11 . 124.18(11) yes
C7  . C10 . F3  . 112.32(13) yes
C7  . C10 . F1  . 111.08(12) yes
F3  . C10 . F1  . 106.31(14) yes
C7  . C10 . F2  . 112.75(14) yes
F3  . C10 . F2  . 106.52(14) yes
F1  . C10 . F2  . 107.49(14) yes
C9  . C11 . C12 . 119.62(12) yes
C9  . C11 . C16 . 121.65(12) yes
C12 . C11 . C16 . 118.73(12) yes
C11 . C12 . C13 . 120.11(13) yes
C11 . C12 . H121. 119.3     no
C13 . C12 . H121. 120.6     no
C12 . C13 . C14 . 121.42(13) yes
C12 . C13 . H131. 118.9     no
C14 . C13 . H131. 119.7     no
C13 . C14 . C15 . 118.23(13) yes
C13 . C14 . C17 . 121.76(15) yes
C15 . C14 . C17 . 120.00(15) yes
C14 . C15 . C16 . 121.02(14) yes
C14 . C15 . H151. 121.2     no
C16 . C15 . H151. 117.7     no
C11 . C16 . C15 . 120.46(13) yes
C11 . C16 . H161. 119.7     no
C15 . C16 . H161. 119.8     no
C14 . C17 . H171. 111.8     no
C14 . C17 . H172. 110.5     no
H171. C17 . H172. 109.7     no
C14 . C17 . H173. 109.5     no
H171. C17 . H173. 108.9     no
H172. C17 . H173. 106.3     no
S101. C101. C102. 121.18(9)  yes
S101. C101. C106. 118.56(9)  yes
C102. C101. C106. 120.25(11) yes
C101. C102. C103. 119.99(12) yes
C101. C102. H1021. 120.9    no
C103. C102. H1021. 119.1    no
C102. C103. C104. 119.29(11) yes
C102. C103. H1031. 120.1    no
C104. C103. H1031. 120.6    no
N103. C104. C103. 121.31(11) yes
N103. C104. C105. 117.80(11) yes
C103. C104. C105. 120.89(11) yes
C104. C105. C106. 119.72(12) yes
C104. C105. H1051. 117.5    no
C106. C105. H1051. 122.7    no
C101. C106. C105. 119.84(11) yes
C101. C106. H1061. 120.5    no
C105. C106. H1061. 119.7    no
N102. C107. C108. 113.05(12) yes
N102. C107. C110. 120.10(13) yes
C108. C107. C110. 126.82(12) yes
```

```
C107 . C108 . C109  . 104.54(11) yes
C107 . C108 . H1081 . 128.3     no
C109 . C108 . H1081 . 127.1     no
C108 . C109 . N103  . 106.28(11) yes
C108 . C109 . C111  . 128.68(12) yes
N103 . C109 . C111  . 124.97(11) yes
C107 . C110 . F103  . 111.51(13) yes
C107 . C110 . F101  . 112.62(12) yes
F103 . C110 . F101  . 105.98(16) yes
C107 . C110 . F102  . 112.67(16) yes
F103 . C110 . F102  . 105.47(13) yes
F101 . C110 . F102  . 108.12(15) yes
C109 . C111 . C112  . 121.72(12) yes
C109 . C111 . C116  . 119.12(12) yes
C112 . C111 . C116  . 119.14(12) yes
C111 . C112 . C113  . 120.31(13) yes
C111 . C112 . H1121 . 119.6     no
C113 . C112 . H1121 . 120.1     no
C112 . C113 . C114  . 120.72(13) yes
C112 . C113 . H1131 . 118.1     no
C114 . C113 . H1131 . 121.2     no
C113 . C114 . C115  . 118.81(13) yes
C113 . C114 . C117  . 120.44(14) yes
C115 . C114 . C117  . 120.75(14) yes
C114 . C115 . C116  . 120.64(13) yes
C114 . C115 . H1151 . 120.3     no
C116 . C115 . H1151 . 119.0     no
C115 . C116 . C111  . 120.34(13) yes
C115 . C116 . H1161 . 119.9     no
C111 . C116 . H1161 . 119.7     no
C114 . C117 . H1171 . 113.2     no
C114 . C117 . H1172 . 109.0     no
H1171 . C117 . H1172 . 106.5    no
C114 . C117 . H1173 . 111.9     no
H1171 . C117 . H1173 . 108.6    no
H1172 . C117 . H1173 . 107.4    no
```

REFERENCES

1. Remenar, J. F., Am. Pharm.Rev., 2007, 10, 84.
2. Guzman, Hector R., Tawa, Mark, Zhang, Zhong, Ratanabanangkoon, Pasut, Shaw, Paul, Gardner, Colin R., Chen, Hongming, Moreau, Jean Pierre, Almarsson, Orn, and Remenar, Julius F., J. Pharm. Sci., 2007, 96, 2686.
3. Lu, G. W., Hawley, M., Smith, M., Geiger, B. M., Pfund, W, J. Pharm. Sci., 2005, 95, 305.
4. Peterson, M. L., Collier, A. E., Hickey, M. B., Guzman, H. R., Almarsson, O., Organic Crystal Engineering Frontiers in Crystal Engineering, ed. E. R. T. Tieking, J. Vittal and M. Zaworotko, John Wiley & Sons, Ltd., 2010, ch. 3, pp. 67-99.
5. Physicians Desk Reference, electronic library version, MicroMedex (Thompson Healthcare).
6. Paulson, S. K., Vaughan, M. B., Jessen, S. M., Lawal, Y., Gresk, C. J., Yan, B., Maziasz, T. J., Cook, C. S., Karim, A., J. Pharmacol. Exp. Ther., 2001, 297, 638.
7. Gupta, P., Chawla, G., Bansal, A. K., Mol. Pharmacol., 2004, 1, 406.
8. Remenar, J. F., Peterson, M. L., Stephens, P. W., Zhang, Z., Zimenkov, Y., Hickey, M. B., Mol. Pharmacol., 2007, 4, 386.
9. Chen, L. R., Young, V. G., Lechuga-Ballesteros, D., Grant, D. J., J. Pharm. Sci., 1999, 88, 1191.
10. Khankari, R., Chen, L., Grant, D. J., J. Pharm. Sci., 1998, 87, 1052.
11. Davey, R. J., Black, S, N., Logan, D., Maginn, S. J., Fairbrother, J. E., and Grant, D. J. W., J. Chem. Soc., Faraday Trans., 1992, 88, 3461.
12. Thompson, Claire, Davies, Martyn C., Roberts, Clive J., Tendler, Saul J. B., and Wilkinson, Mike J., Int. J. Pharm., 2004, 280, 137.
13. Weissbuch, Isabelle, Lahav, Meir, and Leiserowitz, Leslie, Adv. Cryst. Growth Res., 2001, 381.
14. Vasu Dev, R., Rekha, K. Shashi, Vyas, K., Mohanti, S. B., Kumar, P. Rajender, and Reddy, G. Om, Acta Crystallogr., Sect.C: Cryst. Struct. Commun., 1999, 55, v, IUC990161.
15. Apex2, Version 2 User Manual, M86-E01078, 40 Bruker Analytical X-ray Systems, Madison, Wis., June 2006.
16. Betteridge, P. W.; Carruthers, J. R.; Cooper, R. I.; Prout, K.; Watkin, D. J. J. Appl. Cryst. 2003, 36, 1487.
17. Abu T. M. Serajuddin and M. Pudipeddi, Handbook of Pharmaceutical Salts, Verlag Helvetica Chimica Acta: Zurich and Wiley-VCH: Weinheim, 2002, ch. 6, pp. 138-139.

The invention claimed is:

1. A pentahydrate sodium salt form of celecoxib characterized by the powder x-ray diffraction pattern of FIG. 7.

2. A method of preparing a pentahydrate sodium salt form of celecoxib, comprising:
dissolving celecoxib in 1.0 N NaOH;
adding 0.3% benzyl alcohol; and
allowing said pentahydrate sodium salt form of celecoxib to crystallize.

* * * * *